US012606610B2

(12) United States Patent (10) Patent No.: US 12,606,610 B2
Whitfill et al. (45) Date of Patent: *Apr. 21, 2026

(54) COMPOSITIONS AND METHODS FOR TREATMENT OF NETHERTON SYNDROME WITH LEKTI EXPRESSING RECOMBINANT MICROBES

(71) Applicant: Azitra Inc, Branford, CT (US)

(72) Inventors: Travis Michael Whitfill, Dallas, TX (US); Azim Momin Munivar, New Haven, CT (US)

(73) Assignee: Azitra Inc, Branford, CT (US)

( * ) Notice: Subject to any disclaimer, the term of this patent is extended or adjusted under 35 U.S.C. 154(b) by 211 days.

This patent is subject to a terminal disclaimer.

(21) Appl. No.: 18/234,588

(22) Filed: Aug. 16, 2023

(65) Prior Publication Data

US 2024/0218049 A1 Jul. 4, 2024

Related U.S. Application Data

(63) Continuation of application No. 16/010,051, filed on Jun. 15, 2018, now Pat. No. 11,773,154.

(60) Provisional application No. 62/521,050, filed on Jun. 16, 2017.

(51) Int. Cl.
| | |
|---|---|
| *C07K 14/81* | (2006.01) |
| *A61K 9/00* | (2006.01) |
| *A61K 35/74* | (2015.01) |
| *A61P 17/00* | (2006.01) |
| *C12N 15/74* | (2006.01) |

(52) U.S. Cl.
CPC ........ *C07K 14/8135* (2013.01); *A61K 9/0014* (2013.01); *A61K 35/74* (2013.01); *A61P 17/00* (2018.01); *C07K 14/81* (2013.01); *C07K 14/811* (2013.01); *C12N 15/74* (2013.01); *C12N 15/746* (2013.01)

(58) Field of Classification Search
CPC .. A61K 35/744; A61K 35/745; A61K 35/747; A61K 38/57; A61K 9/0014; A61P 17/00; C07K 14/81; C07K 14/811; C07K 14/8135; C12N 15/746
See application file for complete search history.

(56) References Cited

U.S. PATENT DOCUMENTS

| | | |
|---|---|---|
| 9,737,592 B1 | 8/2017 | Bermudes et al. |
| 10,702,558 B2 | 7/2020 | Munivar et al. |
| 11,773,154 B2 * | 10/2023 | Whitfill ............... A61K 9/0014 |
| | | 424/93.2 |
| 2003/0190637 A1 | 10/2003 | Hovnanian et al. |
| 2014/0341881 A1 | 11/2014 | Deperthes et al. |

FOREIGN PATENT DOCUMENTS

| | | |
|---|---|---|
| DE | 102009010942 A1 | 9/2010 |
| WO | 2001/64747 A1 | 9/2001 |
| WO | 2002/066513 A2 | 8/2002 |
| WO | 2010/097066 A1 | 9/2010 |
| WO | 2015/112081 A1 | 7/2015 |
| WO | 2015/114144 A1 | 8/2015 |
| WO | 2015/184134 A1 | 12/2015 |

OTHER PUBLICATIONS

Deraison C, et al., "LEKTI fragments specifically inhibit KLK5, KLK7, and KLK14 and control desquamation through a pH-dependent interaction" Mol Biol Cell. Sep. 2007 (ePub Jun. 7, 2007); 18(9):3607-19; DOI: 10.1091/mbc.e07-02-0124; PMID: 17596512 (Year: 2007).*

Egelrud T, et al., "hK5 and hK7, two serine proteinases abundant in human skin, are inhibited by LEKTI domain 6" Br J Dermatol Dec. 2005;153(6):1200-3; DOI: 10.1111/j.1365-2133.2005.06834.x; PMID: 16307658 (Year: 2005).*

Bitoun et al., LEKTI proteolytic processing in human primary keratinocytes, tissue distribution and defective expression in Netherton syndrome. Hum Mol Genet. Oct. 1, 2003;12(19):2417-30.

Di et al., Ex-vivo gene therapy restores LEKTI activity and corrects the architecture of Netherton syndrome-derived skin grafts. Mol Ther. Feb. 2011;19(2):408-16.

Kreutzmann et al., Recombinant production, purification and biochemical characterization of domain 6 of LEKTI: a temporary Kazal-type-related serine proteinase inhibitor. J Chromatogr B Analyt Technol Biomed Life Sci. Apr. 15, 2004;803(1):75-81.

Magert et al., LEKTI, a novel 15-domain type of human serine proteinase inhibitor. J Biol Chem. Jul. 30, 1999;274 (31):21499-502.

Stout et al., Recombinant filaggrin is internalized and processed to correct filaggrin deficiency. J Invest Dermatol. Feb. 2014;134(2):423-429.

International Search Report and Written Opinion for Application No. PCT/US2018/037850, dated Sep. 26, 2018, 14 pages.

* cited by examiner

*Primary Examiner* — Aaron J Kosar

(74) *Attorney, Agent, or Firm* — McCarter & English, LLP; Jonathan M. Sparks

(57) ABSTRACT

The present disclosure provides, inter alia, engineered microbes expressing recombinant LEKTI domains that are effective to treat or ameliorate the symptoms of Netherton Syndrome. In certain embodiments, compositions, methods, and kits are provided comprising LEKTI domain expressing microbes.

15 Claims, 10 Drawing Sheets

Specification includes a Sequence Listing.

pKK30-LEKTI-complete (5128 bp)

pJB38

- Shuttle vector between E. coli and Staph spp.
- For chromosomal integration
- Amp resistant in E. coli
- Chl resistant in Staph
- Temperature sensitive above 30 °C

SEQUENCE LISTING

```
Sequence total quantity: 125
SEQ ID NO: 1            moltype =   length =
SEQUENCE: 1
000

SEQ ID NO: 2            moltype =   length =
SEQUENCE: 2
000

SEQ ID NO: 3            moltype =   length =
SEQUENCE: 3
000

SEQ ID NO: 4            moltype =   length =
SEQUENCE: 4
000

SEQ ID NO: 5            moltype =   length =
SEQUENCE: 5
000

SEQ ID NO: 6            moltype =   length =
SEQUENCE: 6
000

SEQ ID NO: 7            moltype =   length =
SEQUENCE: 7
000

SEQ ID NO: 8            moltype =   length =
SEQUENCE: 8
000

SEQ ID NO: 9            moltype = AA  length = 25
FEATURE                Location/Qualifiers
REGION                 1..25
                       note = Description of Unknown: Secretion peptide
source                 1..25
                       mol_type = protein
                       organism = unidentified
SEQUENCE: 9
MKKLAFAITA ASGAAAVLSH HDAEA                                            25

SEQ ID NO: 10           moltype = AA  length = 30
FEATURE                Location/Qualifiers
REGION                 1..30
                       note = Description of Unknown: Secretion peptide
source                 1..30
                       mol_type = protein
                       organism = unidentified
SEQUENCE: 10
WLDNRAFSKK FVPVVMATSV ALFFLNLAFA                                       30

SEQ ID NO: 11           moltype = AA  length = 29
FEATURE                Location/Qualifiers
REGION                 1..29
                       note = Description of Unknown: Secretion peptide
source                 1..29
                       mol_type = protein
```

-continued

```
                         organism = unidentified
SEQUENCE: 11
MAKKFNYKLP SMVALTLFGT AFTAHQANA                              29

SEQ ID NO: 12           moltype = AA  length = 27
FEATURE                 Location/Qualifiers
REGION                  1..27
                        note = Description of Unknown: Secretion peptide
source                  1..27
                        mol_type = protein
                        organism = unidentified
SEQUENCE: 12
MKKRFLSICT MTIAALATTT MVNTSYA                                27

SEQ ID NO: 13           moltype = AA  length = 30
FEATURE                 Location/Qualifiers
REGION                  1..30
                        note = Description of Unknown: Secretion peptide
source                  1..30
                        mol_type = protein
                        organism = unidentified
SEQUENCE: 13
NLKKQSKLIL IFICIFTFFI MIIQSQFLMG                             30

SEQ ID NO: 14           moltype = AA  length = 26
FEATURE                 Location/Qualifiers
REGION                  1..26
                        note = Description of Unknown: Secretion peptide
source                  1..26
                        mol_type = protein
                        organism = unidentified
SEQUENCE: 14
MKIFKLTSLT LAALTLAFPF SHVAQA                                 26

SEQ ID NO: 15           moltype = AA  length = 27
FEATURE                 Location/Qualifiers
REGION                  1..27
                        note = Description of Unknown: Secretion peptide
source                  1..27
                        mol_type = protein
                        organism = unidentified
SEQUENCE: 15
MKKTVIASTL AVSLGIAGYG LSGHEAH                                27

SEQ ID NO: 16           moltype = AA  length = 27
FEATURE                 Location/Qualifiers
REGION                  1..27
                        note = Description of Unknown: Secretion peptide
source                  1..27
                        mol_type = protein
                        organism = unidentified
SEQUENCE: 16
MKKNKFLVYL LSTALITPTF ATQTAFA                                27

SEQ ID NO: 17           moltype = AA  length = 35
FEATURE                 Location/Qualifiers
REGION                  1..35
                        note = Description of Unknown: Secretion peptide
source                  1..35
                        mol_type = protein
                        organism = unidentified
SEQUENCE: 17
MKTRQNKYSI RKFSVGASSI LIAALLFMGG GSAQA                       35

SEQ ID NO: 18           moltype = AA  length = 37
FEATURE                 Location/Qualifiers
REGION                  1..37
                        note = Description of Unknown: Secretion peptide
source                  1..37
                        mol_type = protein
                        organism = unidentified
SEQUENCE: 18
MKNNNETRRF SIRKYTVGVV SIITGITIFV SGQHAQA                     37

SEQ ID NO: 19           moltype = AA  length = 30
FEATURE                 Location/Qualifiers
REGION                  1..30
                        note = Description of Unknown: Secretion peptide
source                  1..30
```

-continued

```
                          mol_type = protein
                          organism = unidentified
SEQUENCE: 19
MKKKLSYMIT IMLAFTLSLA LGLFFNSAHA                              30

SEQ ID NO: 20             moltype = AA   length = 45
FEATURE                   Location/Qualifiers
source                    1..45
                          mol_type = protein
                          organism = Staphylococcus epidermidis
SEQUENCE: 20
MKKRRQGPIN KRVDFLSNKV NKYSIRKFTV GTASILVGAT LMFGA            45

SEQ ID NO: 21             moltype = AA   length = 27
FEATURE                   Location/Qualifiers
source                    1..27
                          mol_type = protein
                          organism = Staphylococcus epidermidis
SEQUENCE: 21
MKKRFLSICT MTIAALATTT MVNTSYA                                 27

SEQ ID NO: 22             moltype = AA   length = 29
FEATURE                   Location/Qualifiers
source                    1..29
                          mol_type = protein
                          organism = Staphylococcus epidermidis
SEQUENCE: 22
MAKKFNYKLP SMVALTLFGT AFTAHQANA                               29

SEQ ID NO: 23             moltype = AA   length = 50
FEATURE                   Location/Qualifiers
source                    1..50
                          mol_type = protein
                          organism = Staphylococcus epidermidis
SEQUENCE: 23
MIKKNNLLTK KKPIANKSNK YAIRKFTVGT ASIVIGAALL FGLGHNEAKA       50

SEQ ID NO: 24             moltype = AA   length = 30
FEATURE                   Location/Qualifiers
source                    1..30
                          mol_type = protein
                          organism = Staphylococcus epidermidis
SEQUENCE: 24
MKPFKLIFIS ALMILIMTNA TPISHLNAQA                              30

SEQ ID NO: 25             moltype = AA   length = 35
FEATURE                   Location/Qualifiers
source                    1..35
                          mol_type = protein
                          organism = Staphylococcus epidermidis
SEQUENCE: 25
MKTRQNKYSI RKFSVGASSI LIAALLFMGG GSAQA                        35

SEQ ID NO: 26             moltype = AA   length = 23
FEATURE                   Location/Qualifiers
source                    1..23
                          mol_type = protein
                          organism = Staphylococcus epidermidis
SEQUENCE: 26
MNKFKFFIVF LILSLVFLQN EYA                                     23

SEQ ID NO: 27             moltype = AA   length = 51
FEATURE                   Location/Qualifiers
source                    1..51
                          mol_type = protein
                          organism = Staphylococcus epidermidis
SEQUENCE: 27
MINKKNNLLT KKKPIANKSN KYAIRKFTVG TASIVIGATL LFGLGHNEAK A     51

SEQ ID NO: 28             moltype = AA   length = 26
FEATURE                   Location/Qualifiers
source                    1..26
                          mol_type = protein
                          organism = Staphylococcus epidermidis
SEQUENCE: 28
MKKIATATIA TAGIATFAFA HHDAQA                                  26

SEQ ID NO: 29             moltype = AA   length = 28
FEATURE                   Location/Qualifiers
```

-continued

```
source                    1..28
                          mol_type = protein
                          organism = Staphylococcus epidermidis
SEQUENCE: 29
MKNFSKFALT SIAALTVASP LVNTEVDA                                                28

SEQ ID NO: 30             moltype = AA  length = 37
FEATURE                   Location/Qualifiers
source                    1..37
                          mol_type = protein
                          organism = Staphylococcus epidermidis
SEQUENCE: 30
MKNNNETRRF SIRKYTVGVV SIITGITIFV SGQHAQA                                      37

SEQ ID NO: 31             moltype = AA  length = 19
FEATURE                   Location/Qualifiers
source                    1..19
                          mol_type = protein
                          organism = Staphylococcus epidermidis
SEQUENCE: 31
MRYLKRITIY ISLLILVSG                                                          19

SEQ ID NO: 32             moltype = AA  length = 20
FEATURE                   Location/Qualifiers
source                    1..20
                          mol_type = protein
                          organism = Staphylococcus epidermidis
SEQUENCE: 32
MKLMNKIIVP VTASALLLGA                                                         20

SEQ ID NO: 33             moltype = AA  length = 40
FEATURE                   Location/Qualifiers
source                    1..40
                          mol_type = protein
                          organism = Staphylococcus epidermidis
SEQUENCE: 33
MKKIDSWLTK HGLKNRLTLV VIVIFIIFLI LLFMFVNLSD                                   40

SEQ ID NO: 34             moltype = AA  length = 19
FEATURE                   Location/Qualifiers
source                    1..19
                          mol_type = protein
                          organism = Staphylococcus epidermidis
SEQUENCE: 34
MKKKALLPLF LGIMIFLAG                                                          19

SEQ ID NO: 35             moltype = AA  length = 28
FEATURE                   Location/Qualifiers
source                    1..28
                          mol_type = protein
                          organism = Staphylococcus epidermidis
SEQUENCE: 35
MKKTVIASTL AVSLGIAGYG LSGHEAHA                                                28

SEQ ID NO: 36             moltype = AA  length = 19
FEATURE                   Location/Qualifiers
source                    1..19
                          mol_type = protein
                          organism = Staphylococcus epidermidis
SEQUENCE: 36
MSKFKSLLLL FGTLILLSG                                                          19

SEQ ID NO: 37             moltype = AA  length = 27
FEATURE                   Location/Qualifiers
source                    1..27
                          mol_type = protein
                          organism = Staphylococcus epidermidis
SEQUENCE: 37
MKKTLVASSL AIGLGVVAGN AGHDAHA                                                 27

SEQ ID NO: 38             moltype = AA  length = 29
FEATURE                   Location/Qualifiers
source                    1..29
                          mol_type = protein
                          organism = Staphylococcus epidermidis
SEQUENCE: 38
MAKKFNYKLP SMVALTLFGT AFTAHQANA                                               29

SEQ ID NO: 39             moltype = AA  length = 30
```

-continued

```
FEATURE             Location/Qualifiers
source              1..30
                    mol_type = protein
                    organism = Staphylococcus epidermidis
SEQUENCE: 39
MKKKLSYMIT IMLAFTLSLA LGLFFNSAHA                                      30

SEQ ID NO: 40       moltype = AA   length = 18
FEATURE             Location/Qualifiers
source              1..18
                    mol_type = protein
                    organism = Staphylococcus epidermidis
SEQUENCE: 40
MHKRLFITLL GFIILLAG                                                   18

SEQ ID NO: 41       moltype = AA   length = 19
FEATURE             Location/Qualifiers
source              1..19
                    mol_type = protein
                    organism = Staphylococcus epidermidis
SEQUENCE: 41
MRYLKRITIY ISLLILVSG                                                  19

SEQ ID NO: 42       moltype = AA   length = 25
FEATURE             Location/Qualifiers
source              1..25
                    mol_type = protein
                    organism = Staphylococcus epidermidis
SEQUENCE: 42
MQKKYITAII GTTALSALAS THAQA                                           25

SEQ ID NO: 43       moltype = AA   length = 22
FEATURE             Location/Qualifiers
source              1..22
                    mol_type = protein
                    organism = Staphylococcus epidermidis
SEQUENCE: 43
MKHSSKIIVF VSFLILTIFI GG                                              22

SEQ ID NO: 44       moltype = AA   length = 20
FEATURE             Location/Qualifiers
source              1..20
                    mol_type = protein
                    organism = Staphylococcus epidermidis
SEQUENCE: 44
MKKWQLVGTT VLGASVLLGA                                                 20

SEQ ID NO: 45       moltype = AA   length = 52
FEATURE             Location/Qualifiers
source              1..52
                    mol_type = protein
                    organism = Staphylococcus epidermidis
SEQUENCE: 45
MGKRRQGPIN KKVDFLPNKL NKYSIRKFTV GTASILLGST LIFGSSSHEA KA             52

SEQ ID NO: 46       moltype = AA   length = 26
FEATURE             Location/Qualifiers
source              1..26
                    mol_type = protein
                    organism = Staphylococcus epidermidis
SEQUENCE: 46
MKKIATATIA TAGIATFAFA HHDAQA                                          26

SEQ ID NO: 47       moltype = AA   length = 45
FEATURE             Location/Qualifiers
source              1..45
                    mol_type = protein
                    organism = Staphylococcus epidermidis
SEQUENCE: 47
MKKRRQGPIN KRVDFLSNKV NKYSIRKFTV GTASILVGAT LMFGA                     45

SEQ ID NO: 48       moltype = AA   length = 27
FEATURE             Location/Qualifiers
source              1..27
                    mol_type = protein
                    organism = Staphylococcus epidermidis
SEQUENCE: 48
MKKRFLSICT MTIAALATTT MVNTSYA                                         27
```

-continued

```
SEQ ID NO: 49           moltype = AA   length = 35
FEATURE                 Location/Qualifiers
source                  1..35
                        mol_type = protein
                        organism = Staphylococcus epidermidis
SEQUENCE: 49
MKTRQNKYSI RKFSVGASSI LIAALLFMGG GSAQA                                35

SEQ ID NO: 50           moltype = AA   length = 28
FEATURE                 Location/Qualifiers
source                  1..28
                        mol_type = protein
                        organism = Staphylococcus epidermidis
SEQUENCE: 50
MKNFSKFALT SIAALTVASP LVNTEVDA                                        28

SEQ ID NO: 51           moltype = AA   length = 17
FEATURE                 Location/Qualifiers
source                  1..17
                        mol_type = protein
                        organism = Staphylococcus epidermidis
SEQUENCE: 51
MKKVLASATI LSLMLVG                                                    17

SEQ ID NO: 52           moltype = AA   length = 22
FEATURE                 Location/Qualifiers
source                  1..22
                        mol_type = protein
                        organism = Staphylococcus epidermidis
SEQUENCE: 52
MKYYGKCISY ISILILTFFI GG                                              22

SEQ ID NO: 53           moltype = AA   length = 22
FEATURE                 Location/Qualifiers
source                  1..22
                        mol_type = protein
                        organism = Staphylococcus epidermidis
SEQUENCE: 53
MKHSSKIIVF VSFLILTIFI GG                                              22

SEQ ID NO: 54           moltype = AA   length = 30
FEATURE                 Location/Qualifiers
source                  1..30
                        mol_type = protein
                        organism = Staphylococcus epidermidis
SEQUENCE: 54
MKPFKLIFIS ALMILIMTNA TPISHLNAQA                                      30

SEQ ID NO: 55           moltype = AA   length = 19
FEATURE                 Location/Qualifiers
source                  1..19
                        mol_type = protein
                        organism = Staphylococcus epidermidis
SEQUENCE: 55
MSKFKSLLLL FGTLILLSG                                                  19

SEQ ID NO: 56           moltype = AA   length = 27
FEATURE                 Location/Qualifiers
source                  1..27
                        mol_type = protein
                        organism = Staphylococcus epidermidis
SEQUENCE: 56
MKKTLVASSL AIGLGVVAGN AGHDAHA                                         27

SEQ ID NO: 57           moltype = AA   length = 19
FEATURE                 Location/Qualifiers
source                  1..19
                        mol_type = protein
                        organism = Staphylococcus epidermidis
SEQUENCE: 57
MHYLKKVTIY ISLLILVSG                                                  19

SEQ ID NO: 58           moltype = AA   length = 25
FEATURE                 Location/Qualifiers
source                  1..25
                        mol_type = protein
                        organism = Staphylococcus epidermidis
SEQUENCE: 58
MQKKYITAII GTTALSALAS THAQA                                           25
```

-continued

```
SEQ ID NO: 59            moltype = AA  length = 22
FEATURE                  Location/Qualifiers
source                   1..22
                         mol_type = protein
                         organism = Staphylococcus epidermidis
SEQUENCE: 59
MKHSKKLLLC ISFLLITFFI GG                                       22

SEQ ID NO: 60            moltype = AA  length = 26
FEATURE                  Location/Qualifiers
source                   1..26
                         mol_type = protein
                         organism = Staphylococcus epidermidis
SEQUENCE: 60
MKKIATATIA TAGIATFAFA HHDAQA                                   26

SEQ ID NO: 61            moltype = AA  length = 19
FEATURE                  Location/Qualifiers
source                   1..19
                         mol_type = protein
                         organism = Staphylococcus epidermidis
SEQUENCE: 61
MRYLKKVTIY ISLLILVSG                                           19

SEQ ID NO: 62            moltype = AA  length = 27
FEATURE                  Location/Qualifiers
source                   1..27
                         mol_type = protein
                         organism = Staphylococcus epidermidis
SEQUENCE: 62
MKKRFLSICT MTIAALATTT MVNTSYA                                  27

SEQ ID NO: 63            moltype = AA  length = 20
FEATURE                  Location/Qualifiers
source                   1..20
                         mol_type = protein
                         organism = Staphylococcus epidermidis
SEQUENCE: 63
MKKWQLVGTT VLGASVLLGA                                          20

SEQ ID NO: 64            moltype = AA  length = 29
FEATURE                  Location/Qualifiers
source                   1..29
                         mol_type = protein
                         organism = Staphylococcus epidermidis
SEQUENCE: 64
MAKKFNYKLP SMVALTLFGT AFTAHQANA                                29

SEQ ID NO: 65            moltype = AA  length = 30
FEATURE                  Location/Qualifiers
source                   1..30
                         mol_type = protein
                         organism = Staphylococcus epidermidis
SEQUENCE: 65
MKKKLSYMIT IMLAFTLSLA LGLFFNSAHA                               30

SEQ ID NO: 66            moltype = AA  length = 18
FEATURE                  Location/Qualifiers
source                   1..18
                         mol_type = protein
                         organism = Staphylococcus epidermidis
SEQUENCE: 66
MHKRLFITLL GFIILLAG                                            18

SEQ ID NO: 67            moltype = AA  length = 22
FEATURE                  Location/Qualifiers
source                   1..22
                         mol_type = protein
                         organism = Staphylococcus epidermidis
SEQUENCE: 67
MRYLKKVTIY ISLLILTIFI GG                                       22

SEQ ID NO: 68            moltype = AA  length = 17
FEATURE                  Location/Qualifiers
source                   1..17
                         mol_type = protein
                         organism = Staphylococcus epidermidis
SEQUENCE: 68
```

-continued

```
MKKVLASATI LSLMLVG                                                                17

SEQ ID NO: 69          moltype = AA  length = 22
FEATURE                Location/Qualifiers
source                 1..22
                       mol_type = protein
                       organism = Staphylococcus epidermidis
SEQUENCE: 69
MKHSKKLLLC ISFLLITVFI SG                                                          22

SEQ ID NO: 70          moltype = AA  length = 22
FEATURE                Location/Qualifiers
source                 1..22
                       mol_type = protein
                       organism = Staphylococcus epidermidis
SEQUENCE: 70
MKHSKKLLLC ISFLLITFFI SG                                                          22

SEQ ID NO: 71          moltype = AA  length = 28
FEATURE                Location/Qualifiers
source                 1..28
                       mol_type = protein
                       organism = Staphylococcus epidermidis
SEQUENCE: 71
MKKTVIASTL AVSLGIAGYG LSGHEAHA                                                    28

SEQ ID NO: 72          moltype = AA  length = 22
FEATURE                Location/Qualifiers
source                 1..22
                       mol_type = protein
                       organism = Staphylococcus epidermidis
SEQUENCE: 72
MKHSKKLLLC ISFLLITIFI SG                                                          22

SEQ ID NO: 73          moltype = AA  length = 40
FEATURE                Location/Qualifiers
source                 1..40
                       mol_type = protein
                       organism = Staphylococcus epidermidis
SEQUENCE: 73
MKKIDSWLTK HGLKNRLTLV VIVIFIIFLI LLFMFVNLSD                                       40

SEQ ID NO: 74          moltype = AA  length = 19
FEATURE                Location/Qualifiers
source                 1..19
                       mol_type = protein
                       organism = Staphylococcus epidermidis
SEQUENCE: 74
MKKKALLPLF LGIMIFLAG                                                              19

SEQ ID NO: 75          moltype = AA  length = 20
FEATURE                Location/Qualifiers
source                 1..20
                       mol_type = protein
                       organism = Staphylococcus epidermidis
SEQUENCE: 75
MKLMNKIIVP VTASALLLGA                                                             20

SEQ ID NO: 76          moltype = AA  length = 35
FEATURE                Location/Qualifiers
source                 1..35
                       mol_type = protein
                       organism = Staphylococcus epidermidis
SEQUENCE: 76
MKTRQNKYSI RKFSVGASSI LIAALLFMGG GSAQA                                            35

SEQ ID NO: 77          moltype = AA  length = 13
FEATURE                Location/Qualifiers
REGION                 1..13
                       note = Description of Unknown: Cell penetrating peptide
source                 1..13
                       mol_type = protein
                       organism = unidentified
SEQUENCE: 77
GRKKRRQRRR PPQ                                                                    13

SEQ ID NO: 78          moltype = AA  length = 27
FEATURE                Location/Qualifiers
REGION                 1..27
```

-continued

```
                        note = Description of Unknown: Cell penetrating peptide
source                  1..27
                        mol_type = protein
                        organism = unidentified
SEQUENCE: 78
GWTLNSAGYL LGKINLKALA ALAKKIL                                               27

SEQ ID NO: 79           moltype = AA  length = 18
FEATURE                 Location/Qualifiers
REGION                  1..18
                        note = Description of Unknown: Cell penetrating peptide
source                  1..18
                        mol_type = protein
                        organism = unidentified
SEQUENCE: 79
KLALKLALKA LKAALKLA                                                         18

SEQ ID NO: 80           moltype = AA  length = 30
FEATURE                 Location/Qualifiers
REGION                  1..30
                        note = Description of Unknown: Cell penetrating peptide
source                  1..30
                        mol_type = protein
                        organism = unidentified
SEQUENCE: 80
WEAKLAKALA KALAKHLAKA LAKALKACEA                                            30

SEQ ID NO: 81           moltype = AA  length = 21
FEATURE                 Location/Qualifiers
REGION                  1..21
                        note = Description of Unknown: Cell penetrating peptide
source                  1..21
                        mol_type = protein
                        organism = unidentified
SEQUENCE: 81
KETWWETWWT EWSQPKKKRK V                                                     21

SEQ ID NO: 82           moltype = AA  length = 9
FEATURE                 Location/Qualifiers
REGION                  1..9
                        note = Description of Unknown: Cell penetrating peptide
source                  1..9
                        mol_type = protein
                        organism = unidentified
SEQUENCE: 82
RRRRRRRRR                                                                   9

SEQ ID NO: 83           moltype = AA  length = 24
FEATURE                 Location/Qualifiers
REGION                  1..24
                        note = Description of Unknown: Cell penetrating peptide
source                  1..24
                        mol_type = protein
                        organism = unidentified
SEQUENCE: 83
LGTYTQDFNK FHTFPQTAIG VGAP                                                  24

SEQ ID NO: 84           moltype = AA  length = 15
FEATURE                 Location/Qualifiers
REGION                  1..15
                        note = Description of Unknown: Cell penetrating peptide
source                  1..15
                        mol_type = protein
                        organism = unidentified
SEQUENCE: 84
RQIKWFQNRR MKWKK                                                            15

SEQ ID NO: 85           moltype = AA  length = 11
FEATURE                 Location/Qualifiers
REGION                  1..11
                        note = Description of Unknown: Cell penetrating peptide
source                  1..11
                        mol_type = protein
                        organism = unidentified
SEQUENCE: 85
YGRKKRRQRR R                                                                11

SEQ ID NO: 86           moltype = AA  length = 18
FEATURE                 Location/Qualifiers
```

-continued

```
REGION                  1..18
                        note = Description of Unknown: Cell penetrating peptide
source                  1..18
                        mol_type = protein
                        organism = unidentified
SEQUENCE: 86
RGGRLSYSRR RFSTSTGR                                                       18

SEQ ID NO: 87           moltype = AA   length = 10
FEATURE                 Location/Qualifiers
REGION                  1..10
                        note = Description of Unknown: Cell penetrating peptide
source                  1..10
                        mol_type = protein
                        organism = unidentified
SEQUENCE: 87
RRLSYSRRRF                                                                10

SEQ ID NO: 88           moltype = AA   length = 12
FEATURE                 Location/Qualifiers
REGION                  1..12
                        note = Description of Unknown: Cell penetrating peptide
source                  1..12
                        mol_type = protein
                        organism = unidentified
SEQUENCE: 88
PIRRRKKLRR LK                                                             12

SEQ ID NO: 89           moltype = AA   length = 12
FEATURE                 Location/Qualifiers
REGION                  1..12
                        note = Description of Unknown: Cell penetrating peptide
source                  1..12
                        mol_type = protein
                        organism = unidentified
SEQUENCE: 89
RRQRRTSKLM KR                                                             12

SEQ ID NO: 90           moltype = AA   length = 15
FEATURE                 Location/Qualifiers
REGION                  1..15
                        note = Description of Unknown: Cell penetrating peptide
source                  1..15
                        mol_type = protein
                        organism = unidentified
SEQUENCE: 90
RRRRNRTRRN RRRVR                                                          15

SEQ ID NO: 91           moltype = AA   length = 19
FEATURE                 Location/Qualifiers
REGION                  1..19
                        note = Description of Unknown: Cell penetrating peptide
source                  1..19
                        mol_type = protein
                        organism = unidentified
SEQUENCE: 91
KMTRAQRRAA ARRNRWTAR                                                      19

SEQ ID NO: 92           moltype = AA   length = 13
FEATURE                 Location/Qualifiers
REGION                  1..13
                        note = Description of Unknown: Cell penetrating peptide
source                  1..13
                        mol_type = protein
                        organism = unidentified
SEQUENCE: 92
TRRQRTRRAR RNR                                                            13

SEQ ID NO: 93           moltype = AA   length = 13
FEATURE                 Location/Qualifiers
REGION                  1..13
                        note = Description of Unknown: Cell penetrating peptide
source                  1..13
                        mol_type = protein
                        organism = unidentified
SEQUENCE: 93
GRKKRRQRRR PPQ                                                            13

SEQ ID NO: 94           moltype = AA   length = 13
```

-continued

```
FEATURE                 Location/Qualifiers
REGION                  1..13
                        note = Description of Unknown: Cell penetrating peptide
source                  1..13
                        mol_type = protein
                        organism = unidentified
SEQUENCE: 94
GRRRRRRRRR PPQ                                                    13

SEQ ID NO: 95           moltype = AA  length = 27
FEATURE                 Location/Qualifiers
REGION                  1..27
                        note = Description of Unknown: Cell penetrating peptide
source                  1..27
                        mol_type = protein
                        organism = unidentified
SEQUENCE: 95
GWTLNSAGYL LGKINLKALA ALAKKIL                                     27

SEQ ID NO: 96           moltype = AA  length = 17
FEATURE                 Location/Qualifiers
REGION                  1..17
                        note = Description of Unknown: Cell penetrating peptide
source                  1..17
                        mol_type = protein
                        organism = unidentified
SEQUENCE: 96
KLALKLALKL ALALKLA                                                17

SEQ ID NO: 97           moltype = AA  length = 27
FEATURE                 Location/Qualifiers
REGION                  1..27
                        note = Description of Unknown: Cell penetrating peptide
source                  1..27
                        mol_type = protein
                        organism = unidentified
SEQUENCE: 97
MGLGLHLLVL AAALQGAWSQ PKKKRKV                                     27

SEQ ID NO: 98           moltype = AA  length = 27
FEATURE                 Location/Qualifiers
REGION                  1..27
                        note = Description of Unknown: Cell penetrating peptide
source                  1..27
                        mol_type = protein
                        organism = unidentified
SEQUENCE: 98
GALFLGWLGA AGSTMGAWSQ PKKKRKV                                     27

SEQ ID NO: 99           moltype = AA  length = 27
FEATURE                 Location/Qualifiers
REGION                  1..27
                        note = Description of Unknown: Cell penetrating peptide
source                  1..27
                        mol_type = protein
                        organism = unidentified
SEQUENCE: 99
GALFLGFLGA AGSTMGAWSQ PKKKRKV                                     27

SEQ ID NO: 100          moltype = AA  length = 27
FEATURE                 Location/Qualifiers
REGION                  1..27
                        note = Description of Unknown: Cell penetrating peptide
source                  1..27
                        mol_type = protein
                        organism = unidentified
SEQUENCE: 100
GALFLGFLGA AGSTMGAWSQ PKSKRKV                                     27

SEQ ID NO: 101          moltype = AA  length = 21
FEATURE                 Location/Qualifiers
REGION                  1..21
                        note = Description of Unknown: Cell penetrating peptide
source                  1..21
                        mol_type = protein
                        organism = unidentified
SEQUENCE: 101
KETWWETWWT EWSQPKKKRK V                                           21
```

-continued

```
SEQ ID NO: 102          moltype = AA   length = 21
FEATURE                 Location/Qualifiers
REGION                  1..21
                        note = Description of Unknown: Cell penetrating peptide
source                  1..21
                        mol_type = protein
                        organism = unidentified
SEQUENCE: 102
KETWFETWFT EWSQPKKKRK V                                             21

SEQ ID NO: 103          moltype = AA   length = 1064
FEATURE                 Location/Qualifiers
REGION                  1..1064
                        note = Description of Unknown: sequence
source                  1..1064
                        mol_type = protein
                        organism = unidentified
SEQUENCE: 103
MKIATVSVLL PLALCLIQDA ASKNEDQEMC HEFQAFMKNG KLFCPQDKKF FQSLDGIMFI  60
NKCATCKMIL EKEAKSQKRA RHLARAPKAT APTELNCDDF KKGERDGDFI CPDYYEAVCG  120
TDGKTYDNRC ALCAENAKTG SQIGVKSEGE CKSSNPEQDV CSAFRPFVRD GRLGCTREND  180
PVLGPDGKTH GNKCAMCAEL FLKEAENAKR EGETRIRRNA EKDFCKEYEK QVRNGRLFCT  240
RESDPVRGPD GRMHGNKCAL CAEIFKQRFS EENSKTDQNL GKAEEKTKVK REIVKLCSQY  300
QNQAKNGILF CTRENDPIRG PDGKMHGNLC SMCQAYFQAE NEEKKKAEAR ARNKRESGKA  360
TSYAELCSEY RKLVRNGKLA CTRENDPIQG PDGKVHGNTC SMCEVFFQAE EEEKKKKEGK  420
SRNKRQSKST ASFEELCSEY RKSRKNGRLF CTRENDPIQG PDGKMHGNTC SMCEAFFQQE  480
ERARAKAKRE AAKEICSEFR DQVRNGTLIC TREHNPVRGP DGKMHGNKCA MCASVFKLEE  540
EEKKNDKEEK GKVEAEKVKR EAVQELCSEY RHYVRNGRLP CTRENDPIEG LDGKIHGNTC  600
SMCEAFFQQE AKEKERAEPR AKVKREAEKE TCDEFRRLLQ NGKLFCTREN DPVRGPDGKT  660
HGNKCAMCKA VFQKENEERK RKEEEDQRNA AGHGSSGGGG GNTQDECAEY REQMKNGRLS  720
CTRESDPVRD ADGKSYNNQC TMCKAKLERE AERKNEYSRS RSNGTGSESG KDTCDEFRSQ  780
MKNGKLICTR ESDPVRGPDG KTHGNKCTMC KEKLEREAAE KKKKEDEDRS NTGERSNTGE  840
RSNDKEDLCR EFRSMQRNGK LICTRENNPV RGPYGKMHIN KCAMCQSIFD REANERKKKD  900
EEKSSSKPSN NAKDECSEFR NYIRNNELIC PRENDPVHGA DGKFYTNKCY MCRAVFLTEA  960
LERAKLQEKP SHVRASQEED SPDSFSSLDS EMCKDYRVLP RIGYLCPKDL KPVCGDDGQT  1020
YNNPCMLCHE NLIRQTNTHI RSTGKCEESS TPGTTAASMP PSDE                    1064

SEQ ID NO: 104          moltype = AA   length = 55
FEATURE                 Location/Qualifiers
REGION                  1..55
                        note = Description of Unknown: sequence
source                  1..55
                        mol_type = protein
                        organism = unidentified
SEQUENCE: 104
KNEDQEMCHE FQAFMKNGKL FCPQDKKFFQ SLDGIMFINK CATCKMILEK EAKSQ        55

SEQ ID NO: 105          moltype = AA   length = 63
FEATURE                 Location/Qualifiers
REGION                  1..63
                        note = Description of Unknown: sequence
source                  1..63
                        mol_type = protein
                        organism = unidentified
SEQUENCE: 105
APTELNCDDF KKGERDGDFI CPDYYEAVCG TDGKTYDNRC ALCAENAKTG SQIGVKSEGE  60
CKS                                                                 63

SEQ ID NO: 106          moltype = AA   length = 62
FEATURE                 Location/Qualifiers
REGION                  1..62
                        note = Description of Unknown: sequence
source                  1..62
                        mol_type = protein
                        organism = unidentified
SEQUENCE: 106
NPEQDVCSAF RPFVRDGRLG CTRENDPVLG PDGKTHGNKC AMCAELFLKE AENAKREGET  60
RI                                                                  62

SEQ ID NO: 107          moltype = AA   length = 67
FEATURE                 Location/Qualifiers
REGION                  1..67
                        note = Description of Unknown: sequence
source                  1..67
                        mol_type = protein
                        organism = unidentified
SEQUENCE: 107
NAEKDFCKEY EKQVRNGRLF CTRESDPVRG PDGRMHGNKC ALCAEIFKQR FSEENSKTDQ  60
NLGKAEE                                                             67
```

```
SEQ ID NO: 108          moltype = AA  length = 62
FEATURE                 Location/Qualifiers
REGION                  1..62
                        note = Description of Unknown: sequence
source                  1..62
                        mol_type = protein
                        organism = unidentified
SEQUENCE: 108
REIVKLCSQY QNQAKNGILF CTRENDPIRG PDGKMHGNLC SMCQAYFQAE NEEKKKAEAR  60
AR                                                                  62

SEQ ID NO: 109          moltype = AA  length = 68
FEATURE                 Location/Qualifiers
REGION                  1..68
                        note = Description of Unknown: sequence
source                  1..68
                        mol_type = protein
                        organism = unidentified
SEQUENCE: 109
ESGKATSYAE LCSEYRKLVR NGKLACTREN DPIQGPDGKV HGNTCSMCEV FFQAEEEEKK  60
KKEGKSRN                                                            68

SEQ ID NO: 110          moltype = AA  length = 59
FEATURE                 Location/Qualifiers
REGION                  1..59
                        note = Description of Unknown: sequence
source                  1..59
                        mol_type = protein
                        organism = unidentified
SEQUENCE: 110
ASFEELCSEY RKSRKNGRLF CTRENDPIQG PDGKMHGNTC SMCEAFFQQE ERARAKAKR   59

SEQ ID NO: 111          moltype = AA  length = 62
FEATURE                 Location/Qualifiers
REGION                  1..62
                        note = Description of Unknown: sequence
source                  1..62
                        mol_type = protein
                        organism = unidentified
SEQUENCE: 111
EAAKEICSEF RDQVRNGTLI CTREHNPVRG PDGKMHGNKC AMCASVFKLE EEEKKNDKEE  60
KG                                                                  62

SEQ ID NO: 112          moltype = AA  length = 62
FEATURE                 Location/Qualifiers
REGION                  1..62
                        note = Description of Unknown: sequence
source                  1..62
                        mol_type = protein
                        organism = unidentified
SEQUENCE: 112
EAVQELCSEY RHYVRNGRLP CTRENDPIEG LDGKIHGNTC SMCEAFFQQE AKEKERAEPR  60
AK                                                                  62

SEQ ID NO: 113          moltype = AA  length = 63
FEATURE                 Location/Qualifiers
REGION                  1..63
                        note = Description of Unknown: sequence
source                  1..63
                        mol_type = protein
                        organism = unidentified
SEQUENCE: 113
EAEKETCDEF RRLLQNGKLF CTRENDPVRG PDGKTHGNKC AMCKAVFQKE NEERKRKEEE  60
DQR                                                                 63

SEQ ID NO: 114          moltype = AA  length = 57
FEATURE                 Location/Qualifiers
REGION                  1..57
                        note = Description of Unknown: sequence
source                  1..57
                        mol_type = protein
                        organism = unidentified
SEQUENCE: 114
GNTQDECAEY REQMKNGRLS CTRESDPVRD ADGKSYNNQC TMCKAKLERE AERKNEY     57

SEQ ID NO: 115          moltype = AA  length = 63
FEATURE                 Location/Qualifiers
REGION                  1..63
```

```
                            note = Description of Unknown: sequence
source                      1..63
                            mol_type = protein
                            organism = unidentified
SEQUENCE: 115
ESGKDTCDEF RSQMKNGKLI CTRESDPVRG PDGKTHGNKC TMCKEKLERE AAEKKKKEDE  60
DRS                                                                63

SEQ ID NO: 116              moltype = AA  length = 63
FEATURE                     Location/Qualifiers
REGION                      1..63
                            note = Description of Unknown: sequence
source                      1..63
                            mol_type = protein
                            organism = unidentified
SEQUENCE: 116
NDKEDLCREF RSMQRNGKLI CTRENNPVRG PYGKMHINKC AMCQSIFDRE ANERKKKDEE  60
KSS                                                                63

SEQ ID NO: 117              moltype = AA  length = 62
FEATURE                     Location/Qualifiers
REGION                      1..62
                            note = Description of Unknown: sequence
source                      1..62
                            mol_type = protein
                            organism = unidentified
SEQUENCE: 117
NNAKDECSEF RNYIRNNELI CPRENDPVHG ADGKFYTNKC YMCRAVFLTE ALERAKLQEK  60
PS                                                                62

SEQ ID NO: 118              moltype = AA  length = 62
FEATURE                     Location/Qualifiers
REGION                      1..62
                            note = Description of Unknown: sequence
source                      1..62
                            mol_type = protein
                            organism = unidentified
SEQUENCE: 118
SLDSEMCKDY RVLPRIGYLC PKDLKPVCGD DGQTYNNPCM LCHENLIRQT NTHIRSTGKC  60
EE                                                                62

SEQ ID NO: 119              moltype = DNA  length = 3192
FEATURE                     Location/Qualifiers
misc_feature                1..3192
                            note = Description of Artificial Sequence: Synthetic
                             polynucleotide
source                      1..3192
                            mol_type = other DNA
                            organism = synthetic construct
SEQUENCE: 119
atgaagatag ccacagtgtc agtgcttctg cccttggctc tttgcctcat acaagatgct  60
gccagtaaga atgaagatca ggaaatgtgc catgaatttc aggcatttat gaaaaatgga  120
aaactgttct gtccccagga taagaaattt tttcaaagtc ttgatggaat aatgttcatc  180
aataaatgtg ccacgtgcaa aatgatactg aaaaagaag caaatcaca gaagagggcc  240
aggcatttag caagagctcc caaggctact gccccaacag agctgaattg tgatgatttt  300
aaaaaaggag aaagagatgg ggattttatc tgtcctgatt attatgaagc tgtttgtggc  360
acagatggga aaacatatga caacagatgt gcactgtgtg ctgagaatgc gaaaaccggg  420
tcccaaattg gtgtaaaaag tgaaggggaa tgtaagagca gtaatccaga gcaggatgta  480
tgcagtgctt ttcggccctt tgttagagat ggaagacttg gatgcacaag ggaaaatgat  540
cctgttcttg gtcctgatgg gaagacgcat ggcaataagt gtgcaatgtg tgctgagctg  600
tttttaaaag aagctgaaaa tgccaagcga gaggtgaaa ctagaattcg acgaaatgct  660
gaaaaggatt tttgcaagga atatgaaaaa caagtgagaa atggaaggct tttttgtaca  720
cgggagagtg atccagtccg tggccctgac ggcaggatgc atggcaacaa atgtgccctg  780
tgtgctgaaa ttttcaagca gcgtttttca gaggaaaaca gtaaaacaga tcaaaatttg  840
ggaaaagctg aagaaaaac taaagttaaa agagaaattg tgaaactctg cagtcaatat  900
caaaatcagg caaagaatgg aatactttc tgtaccagag aaaatgaccc tattcgtggt  960
ccagatggga aaatgcatgg caacttgtgt tccatgtgtc aagcctactt ccaagcagaa  1020
aatgaagaaa agaaaaaggc tgaagcacga gctagaaaca agagaaatc tggaaaagca  1080
acctcatatg cagagctttg cagtgaatat cgaaagcttg tgaggaacgg aaaacttgct  1140
tgcaccagag agaacgatcc tatccagggc ccagatggga aagtgcatgg caacacctgc  1200
tccatgtgtg aggtcttctt ccaagcagaa gaagaagaaa agaaaagaa ggaaggtaaa  1260
tcaagaaaca aaagacaatc taagagtaca gcttcctttg aggagttgtg tagtgaatac  1320
cgcaaatcca ggaaaaacgg acggctttt tgcaccagag agaatgaccc catccagggc  1380
ccagatggaa aaatgcatgg caacacctgc tccatgtgtg aggccttctt tcaacaagaa  1440
gaaagagcaa gagcaaaggc taaaagagaa gctgcaaagg aaatctgcag tgaatttcgg  1500
gaccaagtga ggaatggaac acttatatgc accaggaggc ataatcctgt ccgtggccca  1560
gatggcaaaa tgcatggaaa caagtgtgcc atgtgtgcca gtgtgttcaa acttgaagaa  1620
gaagagaaga aaaatgataa agaagaaaaa gggaaagtcg aggctgaaaa agttaagaga  1680
gaagcagttc aggagctgtg cagtgaatat cgtcattatg tgaggaatgg acgactcccc  1740
```

```
tgtaccagag agaatgatcc tattgagggt ctagatggga aaatccacgg caacacctgc      1800
tccatgtgtg aagccttctt ccagcaagaa gcaaaagaaa aagaaagagc tgaacccaga      1860
gcaaaagtca aaagagaagc tgaaaaggag acatgcgatg aatttcggag acttttgcaa      1920
aatggaaaac ttttctgcac aagagaaaat gatcctgtgc gtggcccaga tggcaagacc      1980
catggcaaca agtgtgccat gtgtaaggca gtcttccaga aagaaaatga ggaaagaaag      2040
aggaaagaag aggaagatca gagaaatgct gcaggacatg gttccagtgg tggtggagga      2100
ggaaacactc aggacgaatg tgctgagtat cgggaacaaa tgaaaaatgg aagactcagc      2160
tgtactcggg agagtgatcc tgtacgtgat gctgatggca aatcgtacaa caatcagtgt      2220
accatgtgta aagcaaaatt ggaaagagaa gcagagagaa aaatgagta ttctcgctcc      2280
agatcaaatg ggactggatc agaatcaggg aaggatacat gtgatgagtt tagaagccaa      2340
atgaaaaatg gaaactcat ctgcactcga gaaagtgacc ctgtccgggg tccagatggc      2400
aagacacatg gcaataagtg tactatgtgt aaggaaaaac tggaaaggga agcagctgaa      2460
aaaaaaaaga aagaggatga agacaggagc aatacaggag aaaggagcaa tacaggagaa      2520
aggagcaatg acaaagagga tctgtgtcgt gaatttcgaa gcatgcagag aaatggaaag      2580
cttatctgca ccagagaaaa taaccctgtt cgaggcccat atggcaagat gcacatcaat      2640
aaatgtgcta tgtgtcagag catctttgat cgagaagcta atgaaagaaa aagaaagat      2700
gaagagaaat caagtagcaa gccctcaaat aatgcaaagg atgagtgcag tgaatttcga      2760
aactatataa ggaacaatga actcatctgc cctagaagaga atgacccagt gcacggtgct      2820
gatggaaagt tctatacaaa caagtgctac atgtgcagag ctgtctttct aacagaagct      2880
ttggaaaggg caaagcttca agaaaagcca tcccatgtta gagcttctca agaggaagac      2940
agcccagact ctttcagttc tctggattct gagatgtgca aagactaccg agtattgccc      3000
aggataggtt atctttgtcc aaaaggattta aagcctgtct gtggtgacga tggccaaacc      3060
tacaacaatc cttgcatgct ctgtcatgaa aacctgatac gccaaacaaa tacacacatc      3120
cgcagtacag ggaagtgtga ggagagcagc accccaggaa ccaccgcagc cagcatgccc      3180
ccgtctgacg aa                                                          3192
```

```
SEQ ID NO: 120          moltype = AA  length = 6
FEATURE                 Location/Qualifiers
REGION                  1..6
                        note = Description of Artificial Sequence: Synthetic 6xHis
                        tag
source                  1..6
                        mol_type = protein
                        organism = synthetic construct
SEQUENCE: 120
HHHHHH                                                                  6

SEQ ID NO: 121          moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 121
AAPF                                                                    4

SEQ ID NO: 122          moltype = DNA  length = 21
FEATURE                 Location/Qualifiers
misc_feature            1..21
                        note = Description of Artificial Sequence: Synthetic
                        oligonucleotide
source                  1..21
                        mol_type = other DNA
                        organism = synthetic construct
SEQUENCE: 122
atgcgtcgta tgcgtcgtat g                                                 21

SEQ ID NO: 123          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 123
gtggtggtgg tggtggtg                                                     18

SEQ ID NO: 124          moltype = DNA  length = 22
FEATURE                 Location/Qualifiers
misc_feature            1..22
                        note = Description of Artificial Sequence: Synthetic
                        oligonucleotide
source                  1..22
                        mol_type = other DNA
                        organism = synthetic construct
SEQUENCE: 124
ttgatatgcc tcctaaattt tt                                                22
```

-continued

```
SEQ ID NO: 125       moltype = DNA  length = 21
FEATURE              Location/Qualifiers
misc_feature         1..21
                     note = Description of Artificial Sequence: Synthetic
                      oligonucleotide
source               1..21
                     mol_type = other DNA
                     organism = synthetic construct
SEQUENCE: 125
taggcgcgcc tattctaatg c                                        21
```

COMPOSITIONS AND METHODS FOR TREATMENT OF NETHERTON SYNDROME WITH LEKTI EXPRESSING RECOMBINANT MICROBES

RELATED APPLICATIONS

This application is a continuation of U.S. application Ser. No. 16/010,051, filed on Jun. 15, 2018, granted, which claims priority to U.S. Provisional Application 62/521,050, filed on Jun. 16, 2017, the entire contents of which are incorporated by reference in its entirety herein.

SEQUENCE LISTING

The instant application contains a Sequence Listing which has been submitted electronically in XML format and is hereby incorporated by reference in its entirety. Said XML copy, created on Mar. 11, 2024, is named 129062-00477_SL.xml and is 135,168 bytes in size.

FIELD OF THE DISCLOSURE

The present disclosure relates to methods, kits, and compositions for treating or ameliorating the effects of Netherton Syndrome using one or more recombinant microorganisms that are genetically modified to express one or more therapeutic LEKTI domains on the skin of a subject.

BACKGROUND OF THE INVENTION

The epidermis, the squamous stratified epithelium of the skin, consists of multiple sublayers and is one of the most important barriers of the body against the outside world. The stratum corneum is the outermost layer of the epidermis and develops as a result of the final anucleated step in keratinocyte differentiation from the cells in nucleated epidermal layers. Although the stratum corneum is recognized as the most important physical barrier, the nucleated epidermal layers are also significant in barrier function (Proksch, Brandner et al. 2008). Together, the skin barrier protects against extensive water loss in one direction (inside-outside barrier) and against the invasion of harmful substances from the environment (outside-inside barrier) (Proksch, Brandner et al, 2008). The maintenance of the barrier is also important for balanced proliferation in the basal layer and preservation of the calcium ion gradient and thus proper epidermal differentiation (Lee, Jeong et al. 2006).

A number of current limitations exist in the treatment of skin. Many treatments, such as topical corticosteroids or biologics, do not treat the underlying issues of deficient intrinsic protein in the epidermis or imbalances in the microbial diversity in the skin. While recombinant proteins represent a promising group of therapeutic agents in the treatment of skin disease, several problems accompany their use in the context of the skin.

Traditional methods purify and concentrate recombinant proteins that are extracted from bacterial systems, and then incorporate such preparations into a delivery system. The purification of recombinant proteins is often a very costly method of obtaining protein. Moreover, a number of problems are associated with these traditional methods, including proteolytic degradation, inefficient delivery, and the need for repeated application overtime to achieve therapeutic effect.

One skin disease that would benefit from improved treatment modalities is Netherton Syndrome (NS). NS is a rare autosomal skin disease manifested as severe skin inflammation and scaling, hair shaft defects, constant allergic symptoms, and immune system problems. Newborns with NS often have red and scaly skin that may leak fluid, which creates a risk of dehydration and infections of the skin or throughout the body. Affected children may also fail to grow at a normal rate. The health of older children and adults with NS typically improves, but those individuals are often underweight and of short stature. Most people with NS also have immune system problems such as food allergies, hay fever, asthma, or eczema.

NS is caused by a loss-of-function defect in the gene SPINK5 (serine protease inhibitor of kazal type 5), which encodes lymphoepithelial kazal type related inhibitor type 5 (LEKTI) protein. LEKTI is a multi-domain serine protease inhibitor that is normally expressed in all stratified epithelial cells and the Hassal corpuscules of the thymus. The SPINK5 gene encoding LEKTI is located on chromosome 5 among a cluster of other SPINK genes (e.g. SPINK6 and SPINK9), and comprises 33 exons encoding 15 inhibitory domains separated by linker regions. SPINK5 stands out among the other SPINK genes for the large number of inhibitory domains it encodes. Additionally, the SPINK5 gene is transcribed into three different transcripts, resulting in three different LEKTI proteins that differ in the C-terminal region; i.e. a 145 kDa full length protein having inhibitory domains D1-D15, a 125 kDa (short) protein having inhibitory domains D1-D12, and a 148 kDa (long) protein having an extended linker region 13.

The LEKTI protein is a Kazal-type-related inhibitor. The Kazal motif is defined by the presence of six cysteine residues positioned at specific distances to allow formation of three disulfide bonds in a 1-5, 2-4, and 3-6 pattern. Two of the domains of LEKTI (D2 and D5) form this six cysteine motif, while other domains share four cysteine residues, which produce a rigid inhibitory loop believed to mimic the substrate of target proteases and inactivate the target protease catalytic site.

The LEKTI protein requires proteolytic cleavage for activation of its inhibitory function against many proteases. Specifically, the full length protein is cleaved into domains D1-D5 and D6-D15. The D6-D15 domains are then further cleaved in multiple steps into D6-D9 and D10-D15, →D6 and D7-D9→D7 and D8-D9→D8. This process results in LEKTI proteins comprising between one and six inhibitory domains, with each protein having different inhibitory functions. For example, the various LEKTI inhibitory fragments can inhibit various kallikrein-related peptidases (KLK) such as KLK5, KLK7, and KLK14.

Defective LEKTI proteins can result from substitution, insertion, or deletion mutation of the SPINK5 gene, often causing nonsense or frameshifts mutations that result in premature termination codons. Other mutations in splicesites bases can lead to abnormal splicing events of the transcribed SPINK5 gene. Thus, many SPINK5 mutations result in the complete absence of LEKTI domain synthesis. LEKTI deficiency or defective LEKTI may result in deregulated protease activity causing skin desquamation and epidermal permeability through impaired epidermal differentiation and lipid metabolism, which leads to a defective skin barrier. Furthermore, unregulated activity of some KLK proteins leads to desmosome cleavage and stratum corneum detachment.

Netherton Syndrome is an orphan disease with no specific treatment available. In view of the foregoing, there is a need for novel therapeutic agents for treatment of NS. The present application is directed to meeting these and other needs.

SUMMARY OF THE INVENTION

According to one aspect, the present disclosure provides a composition for the treatment of a skin disease comprising a microbe genetically modified to express and provide one or more LEKTI protein domains onto the skin of a mammal, wherein the LEKTI protein domains are effective to penetrate one or more layers of the mammal's skin and effective to inhibit serine protease activity of at least one serine protease in or on the mammal's skin.

According to some embodiments, the microbe is adapted to live for a controlled duration on the surface of the mammal's skin to provide a continuous supply of LEKTI protein domains. According to some embodiments, the LEKTI protein domains are effective to ameliorate the symptoms of Netherton Syndrome. In one embodiment, the LEKTI domain is Domain 6.

According to some embodiments, the microbe is genetically modified by transfection/transformation with a recombinant DNA plasmid encoding the LEKTI protein domains. In some embodiments, the LEKTI domains are operably linked to one or more recombinant protein domains that are effective to enhance secretion from the microbe and/or penetration of the mammal's skin. According to some embodiments, at least one LEKTI domain is operably linked to a SecA domain. According to some embodiments, at least one LEKTI domain is operably linked to an RMR domain.

According to some embodiments, at least one LEKTI domain comprises an amino acid sequence according to SEQ ID NO: 1.

According to some embodiments, the microbe is adapted to multiply on the skin of the mammal.

According to some embodiments, expression of at least one LEKTI domain is controlled by an operon and the amount of LEKTI provided to the mammal's skin is proportional to the availability of an extrinsic factor. In some embodiments, the expression of at least one LEKTI domain is controlled by a promoter that is constitutively active.

According to some embodiments, the microbe has been genetically modified by transfection/transformation with a recombinant DNA plasmid encoding the LEKTI protein domains and one or more antibiotic resistance genes.

According to some embodiments, the microbe is selected from the group consisting of *Bifidobacterium, Brevibacterium, Propionibacterium, Lactococcus, Streptococcus, Staphylococcus, Lactobacillus, Enterococcus, Pediococcus, Leuconostoc,* or *Oenococcus,* and mixtures thereof.

According to one aspect, the present disclosure provides a method of treating or ameliorating the effects of a skin disease of a mammal in need thereof comprising providing onto a surface of the skin of the mammal a microbe genetically modified to express one or more LEKTI protein domains, wherein the LEKTI protein domains are effective to penetrate one or more layers of the mammal's skin and effective to inhibit activity of at least one serine protease in or on the mammal's skin.

According to some embodiments, the microbe is adapted to live for a controlled duration on the surface of the mammal's skin to provide a continuous supply of LEKTI protein domains.

According to another aspect, the present disclosure provides a kit for the treatment or amelioration of the effects of a skin disease of a mammal in need thereof comprising (1) a composition comprising a microbe that is genetically modified to express one or more LEKTI protein domains, wherein the LEKTI protein domains are effective to penetrate one or more layers of the mammal's skin and effective to inhibit serine protease activity of at least one serine protease in or on the mammal's skin, and (2) reagents for applying the composition to the skin of the mammal.

According to some embodiments, the microbes are adapted to live for a controlled duration on the surface of the mammal's skin to provide a continuous supply of LEKTI protein domains.

According to one aspect, the present disclosure provides a composition for the treatment of skin disease comprising a microbe comprising pJB38-LEKTI-complete plasmid construct.

According to some embodiments, the microbe is selected from the group consisting of *Bifidobacterium, Brevibacterium, Propionibacterium, Lactococcus, Streptococcus, Staphylococcus, Lactobacillus, Enterococcus, Pediococcus, Leuconostoc,* or *Oenococcus,* and mixtures thereof.

According to one aspect, the present disclosure provides a composition comprising pJB38-LEKTI-complete plasmid construct. In some embodiments, the pJB38-LEKTI-complete plasmid construct is expressed in a microbe selected from the group consisting of *Bifidobacterium, Brevibacterium, Propionibacterium, Lactococcus, Streptococcus, Staphylococcus, Lactobacillus, Enterococcus, Pediococcus, Leuconostoc,* or *Oenococcus,* and mixtures thereof.

BRIEF DESCRIPTION OF THE DRAWINGS

FIG. 7A is a schematic of the experiment that was performed. FIG. 7B is a graph that shows trypsin activity.

FIG. 8A is a schematic of the experiment that was performed. FIG. 8B is a graph that shows trypsin activity.

FIG. 9A is a schematic of the experiment that was performed. FIG. 9B is a graph that shows KLK7 activity.

FIG. 10A is a schematic of the experiment that was performed. FIG. 10B is a graph that shows KLK5 activity.

DETAILED DESCRIPTION OF THE INVENTION

Figure 1:
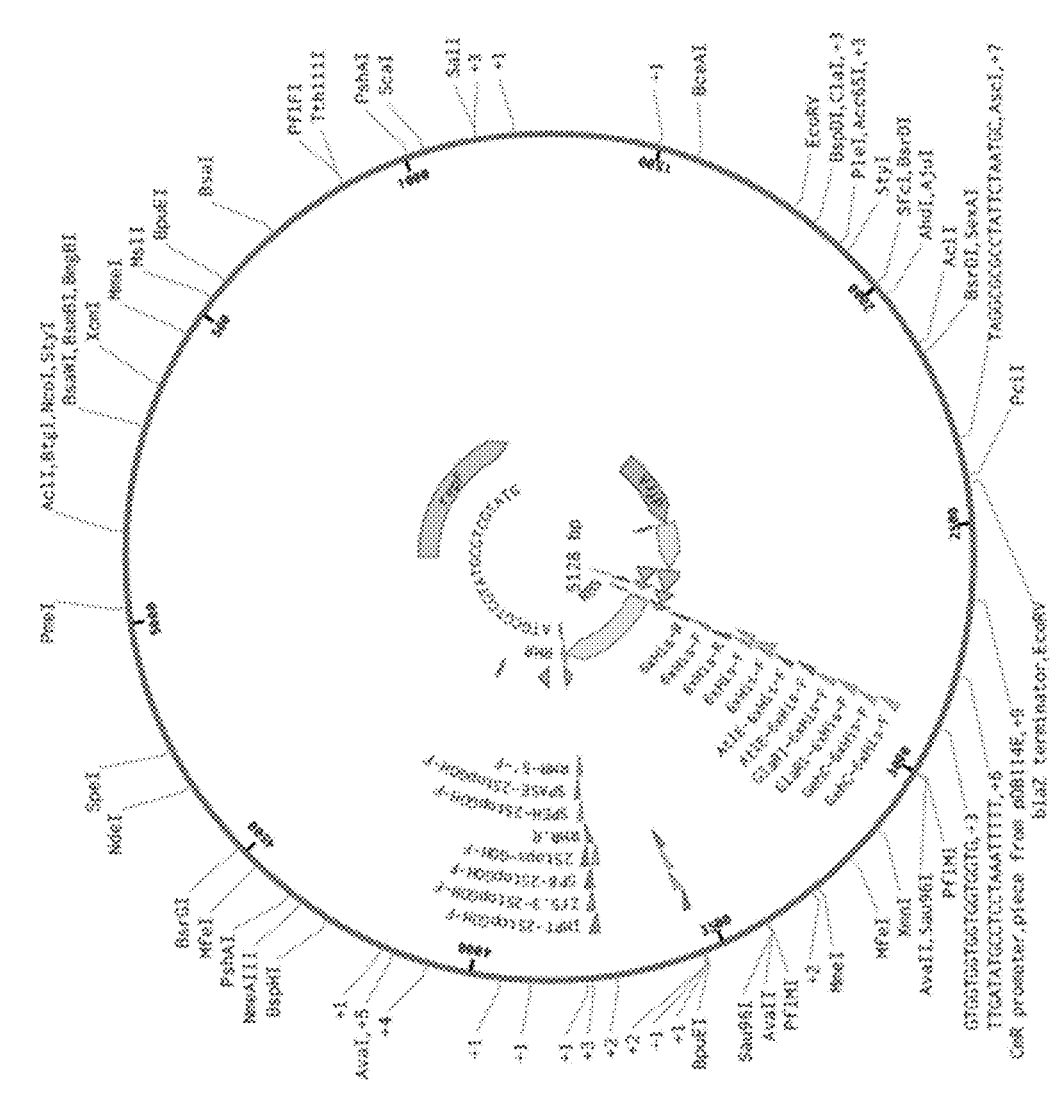
FIG. 1 shows a vector construct comprising the therapeutic LEKTI domains of the present invention. The protein coding regions of the plasmid comprise SecA, 6×His tag, LEKTI D8-11, and RMR tag, operably linked to each other and under the control of a CmR promoter.
Figure 2:
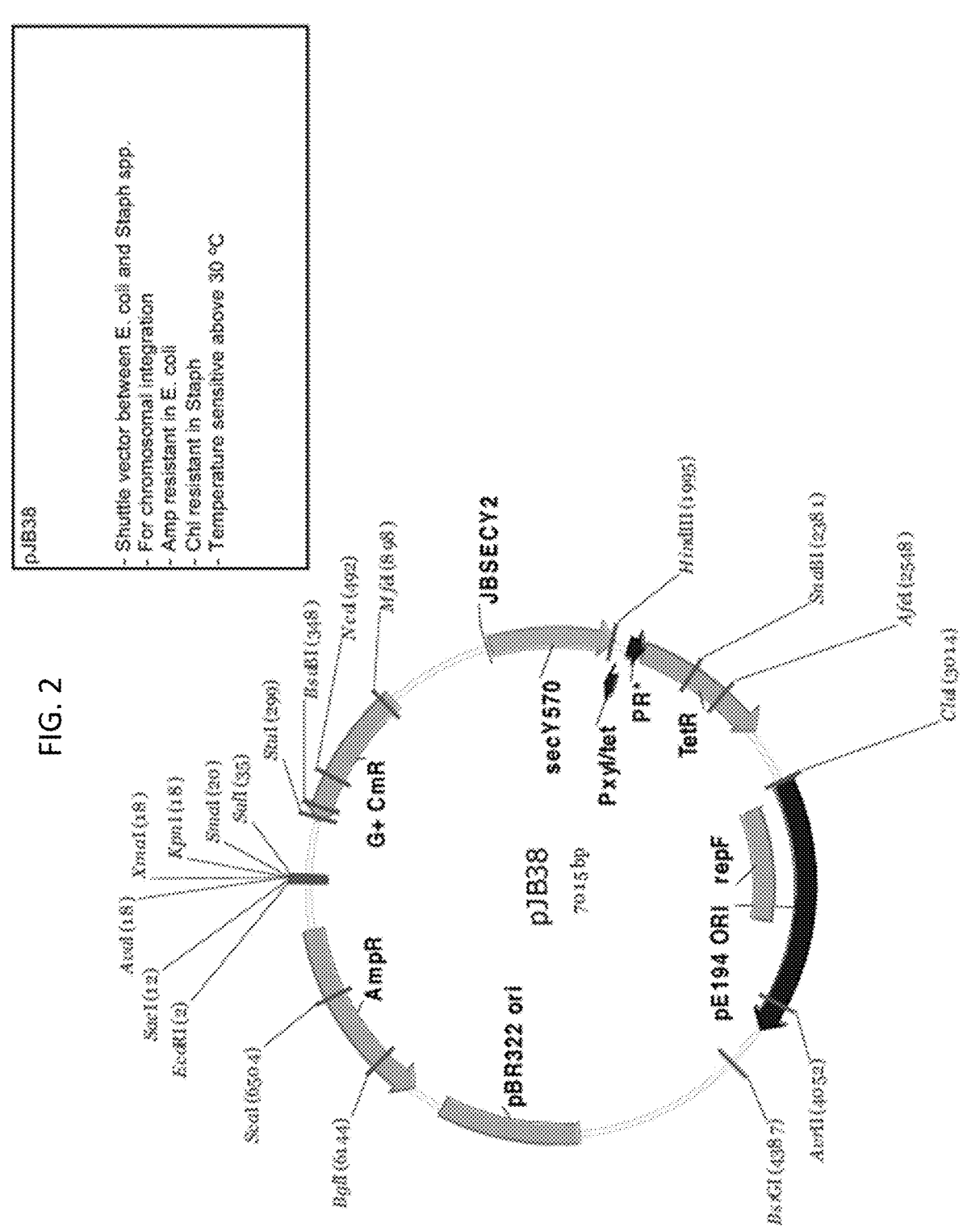
FIG. 2 shows a vector construct of the pJB38 plasmid according to some embodiments of the present invention.

One aspect of the present disclosure provides skin-colonizing bacteria that are genetically altered to express recombinant proteins to treat or ameliorate Netherton Syndrome. The genetically altered protein-producing bacteria are able to treat NS by expressing and, optionally, secreting a therapeutic protein that treats the underlying cause of the disease or its symptoms. According to some embodiments, the therapeutic protein comprises one or more LEKTI domains that are effective to inhibit serine proteases within or on the skin of a mammal. According to some embodiments, the recombinant LEKTI domains compensate for the defective endogenous LEKTI protein naturally produced by the skin in the mammal. According to some embodiments, the genetically altered bacteria are able to self-replicate while retaining the ability to produce the recombinant protein, thereby providing a continuous supply of therapeutic agent.

According to some embodiments, the disclosure provides a composition for the treatment of a skin disease comprising a microbe genetically modified to express and provide one or more LEKTI protein domains onto the skin of a mammal, wherein the LEKTI protein domains are effective to penetrate one or more layers of the mammal's skin and effective to inhibit serine protease activity of at least one serine protease in or on the mammal's skin.

As used herein the term "skin disease" and grammatical variations thereof means a skin state or condition that is generally undesirable or deleterious compared to the normal or baseline condition of human skin. Examples of abnormal skin conditions include, without limitation, Netherton Syndrome, psoriasis, acne, atopic dermatitis, allergic contact dermatitis, epidermolytic hyperkeratosis, seborrheic dermatitis, eczema, dry skin, allergy, rashes, UV-irritated skin, detergent irritated skin (including irritation caused by enzymes and molecules used in washing detergents and sodium lauryl sulfate), thinning skin (e.g. skin from the elderly and children), bullous pemphigoid, pemphigus vulgaris, impetigo, vitiligio, baldness, and hirsutism.

As used herein, the term "genetically modified" and grammatical variations thereof are used to describe a microbial organism (e.g. bacteria) that has been genetically modified or engineered by the introduction of DNA prepared outside the microbe. For example, the introduction of plasmid DNA containing new genes into bacteria will allow the bacteria to express those genes. Alternatively, the DNA containing new genes can be introduced to the bacteria and then integrated into the bacteria's genome, where the bacteria will express those genes.

As used herein, the terms "treat," "treating," "treatment" and grammatical variations thereof mean providing to a subject a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population may fail to respond or respond inadequately to treatment.

In the present invention, the subject may be a mammal. As used herein, a "mammal" and grammatical variations thereof means any category of mammal. In the present invention, mammals include, for example, humans, farm animals, domestic animals, laboratory animals, etc. Some examples of farm animals include cows, pigs, horses, goats, etc. Some examples of domestic animals include dogs, cats, etc. Some examples of laboratory animals include primates, rats, mice, rabbits, guinea pigs, etc. Preferably, the mammal is a human.

As used herein, the term "effective amount" or a "therapeutically effective amount" of a compound or composition disclosed herein is an amount of such compound or composition that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of a composition according to the invention will be that amount of the composition, which is the lowest dose effective to produce the desired effect. The effective dose of a composition of the present invention may be administered as two, three, four, five, six or more sub-doses, administered separately at appropriate intervals throughout the day.

Microbial compositions: According to some embodiments, the disclosure provides microbial compositions comprising one or more of a wide range of bacteria suitable for use on a mammal's skin. Examples include, but are not limited to, non-pathogenic and commensal bacteria. Bacteria suitable for use in the present invention include, but are not limited to, *Bifidobacterium, Brevibacterium, Propionibacterium, Lactococcus, Streptococcus, Staphylococcus* (e.g., *S. epidermidis* and/or *S. hominis*), *Lactobacillus* (e.g., *L. acidophilus*), *Pediococcus, Leuconostoc,* or *Oenococcus.* According to some embodiments, microbial compositions comprise one or more of *Staphylococcus warneri, Streptococcus pyogenes, Streptococcus mitis, Propionibacterium acnes, Corynebacterium* spp., *Acinetobacter johnsonii, Pseudomonas aeruginosa.* According to some embodiments, other related or similar species found on the skin are used.

Certain embodiments involve the use of bacterium *Staphylococcus epidermidis.* According to some embodiments, the strain of *S. epidermidis* to be used is incapable of producing biofilms. An example of this is *S. epidermidis* strain ATCC 12228 or NRRL B-4268.

According to some embodiments, the recombinant microbe is adapted to live indefinitely or for a controlled duration on the surface of the mammal's skin to provide a continuous supply of LEKTI protein domains. In some embodiments, the recombinant microbe lives alongside commensal microorganisms naturally occurring on the mammal's skin. In some embodiments, the recombinant microbe lives to the exclusion of commensal microorganisms that naturally occur on the mammal's skin. According to some embodiments, the recombinant microbe is adapted to multiply on the skin of the mammal. In other embodiments, the recombinant microbe is no longer alive, but contains effective amounts of a therapeutic polypeptide, e.g. LEKTI or therapeutically effective domain(s) thereof. Such cells may be intact or not depending upon the particulars of delivering the therapeutic peptide (or domain(s) thereof) to the target site.

As used herein, the term "recombinant" and grammatical variations thereof means relating to or denoting an organism, protein, or genetic material formed by or using recombined DNA comprising DNA pieces from different sources or from different parts of the same source. For example, the term "recombinant DNA" means a DNA molecule formed through recombination methods to splice fragments of DNA from a different source or from different parts of the same source. In some embodiments, two or more different sources of DNA are cleaved using restriction enzymes and joined together using ligases. As another example, the term "recombinant protein" or "recombinant domains" and grammatical variations thereof means a protein molecule formed through recombination methods originating from spliced fragments of DNA from a different source or from different parts of the same source. As another example, the term "recombinant microbe" or "recombinant bacteria" and grammatical variations thereof mean a microbe/bacteria that comprises one or more recombinant DNA/protein molecules.

According to some embodiments, the microbe is selected from the group consisting of *Bifidobacterium, Brevibacterium, Propionibacterium, Lactococcus, Streptococcus, Staphylococcus* (e.g., *S. epidermidis* and/or *S. hominis*), *Lactobacillus* (e.g., *L. acidophilus*), *Enterococcus, Pediococcus, Leuconostoc,* or *Oenococcus,* and mixtures thereof.

LEKTI gene: According to some embodiments, the recombinant microbe is engineered to express a mammalian gene encoding LEKTI protein. The LEKTI gene can be obtained from any mammal, such as mouse, rat, rabbit, goat, sheep, horse, cow, dog, primate, or human gene sequences. According to some embodiments, the LEKTI gene sequence is a human gene sequence. According to some embodiments, the recombinant microbe is engineered to comprise a fragment of the LEKTI gene.

According to some embodiments, the recombinant protein expressed by the engineered microbe comprises the peptide sequence according to SEQ ID NO: 1 (LEKTI D8-11). According to some embodiments, the recombinant protein expressed by the engineered microbe comprises the peptide sequence according to SEQ ID NO: 2. According to some embodiments, one or more fragments of the peptide sequence according to SEQ ID NO: 2 are expressed by the engineered microbe. In one embodiment, the fragment comprises one or more LEKTI domains. In a specific embodiment, the LEKTI domain is Domain 6.

According to some embodiments, the recombinant microbe comprises a sequence as disclosed herein that has at least about 75% identity, or 80% identity, or 85% identity, or 90% identity, or 95% identity to any one or more of the SEQ ID NOS listed herein. As used herein, the term "identity" and grammatical versions thereof means the extent to which two nucleotide or amino acid sequences have the same residues at the same positions in an alignment. Percent (%) identity is calculated by multiplying the number of matches in a sequence alignment by 100 and dividing by the length of the aligned region, including internal gaps.

According to some embodiments, the recombinant protein expressed by the engineered microbe comprises one or more protease inhibitory domains of the LEKTI protein. Some non-limiting examples include one or more of domains D1, D2, D3, D4, D5, D6, D7, D8, D9, D10, D11, D12, D13, D14, and D15. According to some embodiments, the recombinant protein expressed by the engineered microbe comprises LEKTI inhibitory domain 6 or domains D8 to D11.

According to some embodiments, the LEKTI protein domains are effective to ameliorate the symptoms of Netherton Syndrome. As used herein, the terms "ameliorate", "ameliorating" and grammatical variations thereof mean to decrease the severity of the symptoms of a disease in a subject. In some embodiments, the LEKTI protein domains act as a competitive or non-competitive inhibitor of one or more proteases present on or in the skin of a mammal. In some embodiments, the LEKTI protein domain acts as a serine protease inhibitor. As used herein, the terms "protease" and "proteinase" are used interchangeably, with both terms referring to an enzyme that performs proteolysis.

According to some embodiments, the microbe is genetically modified by transfection/transformation with a recombinant DNA plasmid encoding the LEKTI protein domains. Other conventional or to-be-discovered methods for introducing DNA into a microbe may also be used in the present invention. According to some embodiments, the recombinant DNA plasmid comprises sequences encoding the LEKTI protein domain and one or more secretory peptides and/or cell penetration peptides. According to some embodiments, the LEKTI domains are operably linked to one or more recombinant protein domains that are effective to enhance secretion from the microbe and/or penetration of the mammal's skin.

The term "operably linked" refers to the association of nucleic acid sequences on a single nucleic acid fragment so that the function of one is regulated by the other or is not hindered by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, two proteins can be operably linked, such that the function of either protein is not compromised. Generally, operably linked means that the nucleic acid sequences being linked are contiguous and, where necessary to join two protein coding regions, contiguous and in the same reading frame.

As used herein the term "secretory peptides" or "secretory sequences" or "secretion tags" or "signal peptides" or "export signals" and grammatical variations thereof means any peptide sequence that is capable of targeting the synthesized protein to the secretory pathway of a cell. In some embodiments, the secretory peptide may be positioned on the N-terminal end of a recombinant protein, and may co-translationally or post-translationally target the tagged protein for secretion. According to some embodiments, at least one LEKTI domain is operably linked to a SecA domain (SEQ ID NO: 3).

Secretion peptides: According to some embodiments, the therapeutic LEKTI domain is operably linked to one or more secretion signals or export signals that tag the protein for transport through the secretory pathway. Any secretion signal that facilitates exit of the LEKTI protein out of the bacterial cell may be used as a secretion peptide. Non-limiting examples of secretion peptides signals are set forth in Table 1, below:

TABLE 1

| Amino Acid Sequence | SEQ ID NO: |
|---|---|
| MKKLAFAITAASGAAAVLSHHDAEA | 9 |
| WLDNRAFSKKFVPVVMATSVALFFLNLAFA | 10 |
| MAKKFNYKLPSMVALTLFGTAFTAHQANA | 11 |
| MKKRFLSICTMTIAALATTTMVNTSYA | 12 |
| NLKKQSKLILIFICIFTFFIMIIQSQFLMG | 13 |
| MKIFKLTSLTLAALTLAFPFSHVAQA | 14 |
| MKKTVIASTLAVSLGIAGYGLSGHEAH | 15 |
| MKKNKFLVYLLSTALITPTFATQTAFA | 16 |

TABLE 1-continued

| Amino Acid Sequence | SEQ ID NO: |
|---|---|
| MKTRQNKYSIRKFSVGASSILIAALLFMGGGSAQA | 17 |
| MKNNNETRRFSIRKYTVGVVSIITGITIFVSGQHAQA | 18 |
| MKKKLSYMITIMLAFTLSLALGLFFNSAHA | 19 |

According to some embodiments, the therapeutic LEKTI domain is operably linked to one or more signal sequences derived from endogenous proteins of *Staphylococcus epidermidis*. Non-limiting examples of secretion signal peptides derived from endogenous proteins of *Staphylococcus epidermidis* are set forth in Table 2 below:

TABLE 2

| | | *Staphylococcus epidermidis* | |
|---|---|---|---|
| Protein Name | Amino Acid Length | Signal Sequence | SEQ ID NO |
| Serine-aspartate repeat-containing protein F | 45 | MKKRRQGPINKRVDFLSNKVNK YSIRKFTVGTASILVGATLMFGA | 20 |
| Glutamyl endopeptidase | 27 | MKKRFLSICTMTIAALATTTMVN TSYA | 21 |
| Bifunctional autolysin | 29 | MAKKFNYKLPSMVALTLFGTAF TAHQANA | 22 |
| Serine-aspartate repeat-containing protein G | 50 | MIKKNNLLTKKKPIANKSNKYAI RKFTVGTASIVIGAALLFGLGHN EAKA | 23 |
| Biofilm PIA synthesis deacetylase icaB | 30 | MKPFKLIFISALMILIMTNATPISH LNAQA | 24 |
| Lipase | 35 | MKTRQNKYSIRKFSVGASSILIAA LLFMGGGSAQA | 25 |
| Epidermin leader peptide-processing serine protease epiP | 23 | MNKFKFFIVFLILSLVFLQNEYA | 26 |
| Fibrinogen-binding protein | 51 | MINKKNNLLTKKKPIANKSNKY AIRKFTVGTASIVIGATLLFGLGH NEAK A | 27 |
| Staphylococcal secretory antigen ssaA | 26 | MKKIATATIATAGIATFAFAHHD AQA | 28 |
| Extracellular elastase | 28 | MKNFSKFALTSIAALTVASPLVN TEVDA | 29 |
| n/a | 37 | MKNNNETRRFSIRKYTVGVVSIIT GITIFVSGQHAQA | 30 |

TABLE 2-continued

| Protein Name | Amino Acid Length | Signal Sequence | SEQ ID NO |
|---|---|---|---|
| *Staphylococcus epidermidis* | | | |
| Uncharacterized lipoprotein SE_0145 | 19 | MRYLKRITIYISLLILVSG | 31 |
| Foldase protein prsA | 20 | MKLMNKIIVPVTASALLLGA | 32 |
| Probable cell wall amidase lytH | 40 | MKKIDSWLTKHGLKNRLTLVVI VIFIIFLILLFMFVNLSD | 33 |
| Membrane protein oxaA 2 | 19 | MKKKALLPLFLGIMIFLAG | 34 |
| Probable transglycosylase isaA | 28 | MKKTVIASTLAVSLGIAGYGLSG HEAHA | 35 |
| Probable quinol oxidase subunit 2 | 19 | MSKFKSLLLLFGTLILLSG | 36 |
| Probable transglycosylase sceD | 27 | MKKTLVASSLAIGLGVVAGNAG HDAHA | 37 |
| Bifunctional autolysin | 29 | MAKKFNYKLPSMVALTLFGTAF TAHQANA | 38 |
| Extracellular cysteine protease | 30 | MKKKLSYMITIMLAFTLSLALGL FFNSAHA | 39 |
| Membrane protein oxaA 1 | 18 | MHKRLFITLLGFIILLAG | 40 |
| Uncharacterized lipoprotein SE_0144 | 19 | MRYLKRITIYISLLILVSG | 41 |
| N-acetylmuramoyl-L-alanine amidase sle1 | 25 | MQKKYITAIIGTTALSALASTHA QA | 42 |
| Uncharacterized lipoprotein SE_0142 | 22 | MKHSSKIIVFVSFLILTIFIGG | 43 |
| Phosphate-binding protein pstS | 20 | MKKWQLVGTTVLGASVLLGA | 44 |
| Accumulation-associated protein | 52 | MGKRRQGPINKKVDFLPNKLNK YSIRKFTVGTASILLGSTLIFGSSS HEAKA | 45 |
| Staphylococcal secretory antigen ssaA | 26 | MKKIATATIATAGIATFAFAHHD AQA | 46 |
| Serine-aspartate repeat-containing protein F | 45 | MKKRRQGPINKRVDFLSNKVNK YSIRKFTVGTASILVGATLMFGA | 47 |
| Glutamyl endopeptidase | 27 | MKKRFLSICTMTIAALATTTMVN TSYA | 48 |

TABLE 2-continued

*Staphylococcus epidermidis*

| Protein Name | Amino Acid Length | Signal Sequence | SEQ ID NO |
|---|---|---|---|
| Lipase | 35 | MKTRQNKYSIRKFSVGASSILIAA LLFMGGGSAQA | 49 |
| Extracellular elastase | 28 | MKNFSKFALTSIAALTVASPLVN TEVDA | 50 |
| Uncharacterized lipoprotein SE_1947 | 17 | MKKVLASATILSLMLVG | 51 |
| Uncharacterized lipoprotein SE_0186/SE_0187 | 22 | MKYYGKCISYISILILTFFIGG | 52 |
| Uncharacterized lipoprotein SERP2423 | 22 | MKHSSKIIVFVSFLILTIFIGG | 53 |
| Biofilm PIA synthesis deacetylase icaB | 30 | MKPFKLIFISALMILIMTNATPISH LNAQA | 54 |
| Probable quinol oxidase subunit 2 | 19 | MSKFKSLLLLFGTLILLSG | 55 |
| Probable transglycosylase sceD | 27 | MKKTLVASSLAIGLGVVAGNAG HDAHA | 56 |
| Uncharacterized lipoprotein SERP2447 | 19 | MHYLKKVTIYISLLILVSG | 57 |
| N-acetylmuramoyl-L-alanine amidase sle1 | 25 | MQKKYITAIIGTTALSALASTHA QA | 58 |
| Uncharacterized lipoprotein SERP2445 | 22 | MKHSKKLLLCISFLLITFFIGG | 59 |
| Staphylococcal secretory antigen ssaA | 26 | MKKIATATIATAGIATFAFAHHD AQA | 60 |
| Uncharacterized lipoprotein SERP2443 | 19 | MRYLKKVTIYISLLILVSG | 61 |
| Glutamyl endopeptidase | 27 | MKKRFLSICTMTIAALATTTMVN TSYA | 62 |
| Phosphate-binding protein pstS | 20 | MKKWQLVGTTVLGASVLLGA | 63 |
| Bifunctional autolysin | 29 | MAKKFNYKLPSMVALTLFGTAF TAHQANA | 64 |
| Extracellular cysteine protease | 30 | MKKKLSYMITIMLAFTLSLALGL FFNSAHA | 65 |
| Membrane protein oxaA 1 | 18 | MHKRLFITLLGFIILLAG | 66 |

TABLE 2-continued

| | Staphylococcus epidermidis | | |
| --- | --- | --- | --- |
| Protein Name | Amino Acid Length | Signal Sequence | SEQ ID NO |
| Uncharacterized lipoprotein SERP2422 | 22 | MRYLKKVTIYISLLILTIFIGG | 67 |
| Uncharacterized lipoprotein SERP1959 | 17 | MKKVLASATILSLMLVG | 68 |
| Uncharacterized lipoprotein SERP2453 | 22 | MKHSKKLLLCISFLLITVFISG | 69 |
| Uncharacterized lipoprotein SERP2465 | 22 | MKHSKKLLLCISFLLITFFISG | 70 |
| Probable transglycosylase isaA | 28 | MKKTVIASTLAVSLGIAGYGLSG HEAHA | 71 |
| Uncharacterized lipoprotein SERP2451 | 22 | MKHSKKLLLCISFLLITIFISG | 72 |
| Probable cell wall amidase lytH | 40 | MKKIDSWLTKHGLKNRLTLVVI VIFIIFLILLFMFVNLSD | 73 |
| Membrane protein oxaA 2 | 19 | MKKKALLPLFLGIMIFLAG | 74 |
| Foldase protein prsA | 20 | MKLMNKIIVPVTASALLLGA | 75 |
| Lipase | 35 | MKTRQNKYSIRKFSVGASSILIAA LLFMGGGSAQA | 76 |

According to some embodiments, the therapeutic LEKTI domain is operably linked to one or more secretion signal sequences derived from endogenous proteins of other bacteria. Non-limiting examples of secretion signal peptides derived from endogenous proteins of various bacteria are set forth in Appendix A.

According to some embodiments, the recombinant LEKTI domain is operably linked to a cell penetration peptide sequence that enhances the ability of the LEKTI domain to pass through a cell membrane. The term "enhance" as used to describe the cell penetration peptide/ LEKTI, means that the cell penetration sequence improves the passage of recombinant LEKTI domain through a cell membrane relative to a recombinant LEKTI domain lacking the cell penetration sequence.

Cell penetration peptides: According to some embodiments, one or more cell penetrating peptides are used to mediate delivery of therapeutic proteins in vivo without using cell surface receptors and without causing significant membrane damage. According to some embodiments, one or more cell penetrating peptides are operably linked to therapeutic proteins to facilitate entry into skin cells (e.g. keratinocytes). Non-limiting examples are set forth in Table 3, below:

TABLE 3

| Cell penetrating sequence | SEQ ID NO |
| --- | --- |
| GRKKRRQRRRPPQ | 77 |
| GWTLNS AGYLLGKINLKALAALAKKIL | 78 |
| KLALKLALKALKAALKLA | 79 |
| WEAKLAKALAKALAKHLAKALAKALKACEA | 80 |
| KETWWETWWTEWSQPKKKRKV | 81 |
| RRRRRRRRR | 82 |
| LGTYTQDFNKFHTFPQTAIGVGAP | 83 |
| RQIKWFQNRRMKWKK | 84 |
| YGRKKRRQRRR | 85 |
| RGGRLSYSRRRFSTSTGR | 86 |
| RRLSYSRRRF | 87 |
| PIRRRKKLRRLK | 88 |
| RRQRRTSKLMKR | 89 |
| RRRRNRTRRNRRRVR | 90 |

TABLE 3-continued

| Cell penetrating sequence | SEQ ID NO |
| --- | --- |
| KMTRAQRRAAARRNRWTAR | 91 |
| TRRQRTRRARRNR | 92 |
| GRKKRRQRRRPPQ | 93 |
| GRRRRRRRRRPPQ | 94 |
| GWTLNSAGYLLGKINLKALAALAKKIL | 95 |
| KLALKLALKLALALKLA | 96 |
| MGLGLHLLVLAAALQGAWSQPKKKRKV | 97 |
| GALFLGWLGAAGSTMGAWSQPKKKRKV | 98 |
| GALFLGFLGAAGSTMGAWSQPKKKRKV | 99 |
| GALFLGFLGAAGSTMGAWSQPKSKRKV | 100 |
| KETWWETWWTEWSQPKKKRKV | 101 |
| KETWFETWFTEWSQPKKKRKV | 102 |

According to some embodiments, cell penetrating peptides comprise periodic amino acid sequences. Non-limiting examples of periodic cell penetrating sequences include: Polyarginines, R×n (wherein 4<n<17); Polylysines, K×n (wherein 4<n<17); arginine repeats interspaced with 6-aminocaprotic acid residues (RAca), wherein there are 2 to 6 arginine repeats; arginine repeats interspaced with 4-aminobutyric acid (RAbu), wherein there are 2 to 6 arginine repeats; arginine repeats interspaced with methionine, wherein there are 2 to 6 arginine repeats; arginine repeats interspaced with threonine, wherein there are 2 to 6 arginine repeats; arginine repeats interspaced with serine, wherein there are 2 to 6 arginine repeats; and arginine repeats interspaced with alanine, wherein there are 2 to 6 arginine repeats.

According to some embodiments, the LEKTI domain is operably linker to an RMR domain (SEQ ID NO: 4).

According to some embodiments, expression of the LEKTI domain is controlled by an operon and the amount of LEKTI provided to the mammal's skin is proportional to the availability of an extrinsic factor. For example, in some embodiments the recombinant LEKTI gene may be under the control of a xylose inducible promoter (e.g. xylose repressor (xylR), xylose operator (xylO), xylose isomerase gene (xylA) including the cis-acting catabolite-responsive element (CRE)), and the amount of recombinant LEKTI protein made available to the skin of the mammal controlled by the amount of exogenous xylose available to the recombinant microbe. According to some embodiments, the expression of the LEKTI domain is controlled by a promoter that is constitutively active. According to some embodiments, the expression of the LEKTI domain is controlled by a CmR promoter according to SEQ ID NO: 8.

According to some embodiments, the microbe is genetically modified by transfection/transformation with a recombinant DNA plasmid encoding the LEKTI protein domains and one or more antibiotic resistance genes. For example, some embodiments of the recombinant DNA plasmid comprise a kanamycin resistance gene and/or a trimethoprim resistance gene; e.g. dfrA (SEQ ID NO: 5). According to some embodiments, treatment of the skin of the mammal with an antibiotic (for which the recombinant microbe is resistant) may be used to bias the population of commensal microbes toward a larger proportion of LEKTI producing microbes. Other elements that may be present in the recombinant DNA plasmid include, without limitation, a replication protein gene, such as a member of the Rep superfamily of replication proteins. For example, in some embodiments the recombinant DNA plasmid comprises the repF gene (SEQ ID NO: 6).

According to some embodiments, the recombinant DNA plasmid comprises one or more sequences of the pJB38 vector. In some embodiments, the recombinant LEKTI is operably linked to an inducible promoter, ribosome binding site, export signal, and/or cell penetrating peptide in the pJB38 vector. As used herein, the term "pJB38-LEKTI-complete" means a recombinant DNA plasmid construct comprising the pJB38 vector and one or more LEKTI domains. According to some embodiments, the recombinant DNA plasmid comprises the pJB38 vector according to SEQ ID NO: 1542. According to some embodiments, the LEKTI domain according to SEQ ID NO: 1 is operably linked to the pJB38 vector according to SEQ ID NO: 1542.

According to some embodiments, the recombinant DNA plasmid comprises the pKK30-LEKTI-complete sequence according to SEQ ID NO: 7 (Appendix B). According to some embodiments, the present disclosure provides a composition for the treatment of a skin disease comprising a microbe comprising the pKK30-LEKTI-complete plasmid construct. According to some such embodiments, the microbe is selected from the group consisting of *Bifidobacterium, Brevibacterium, Propionibacterium, Lactococcus, Streptococcus, Staphylococcus* (e.g., *S. epidermidis* and/or *S. hominis*), *Lactobacillus* (e.g., *L. acidophilus*), *Enterococcus, Pediococcus, Leuconostoc*, or *Oenococcus*, and mixtures thereof.

According to some embodiments, the amount or durations of availability of therapeutic LEKTI protein is controlled by the stability of the vector harboring the LEKTI in a microbe. For example, the persistence of a recombinant vector may be controlled by one or more elements of a plasmid including those that provide host-beneficial genes, plasmid stability mechanisms, and plasmid co-adaptation. For example, some plasmid may provide for stable replication, active partitioning mechanisms, and mechanisms that insure reliable inheritance of plasmids to daughter cells over generations. (See, e.g., J. C. Baxter, B. E. Funnell, Plasmid partition mechanisms, Microbiol. Spectr., 2 (2014) PLAS-0023-2014 and Nils Hülter et al., An evolutionary perspective on plasmid lifestyle modes, Current Opinion in Microbiology, Volume 38, August 2017, Pages 74-80, each of which are incorporated by herein by reference in its entirety) According to some embodiments, the present invention includes the use of all conventional selection and stability methods known to a person of skill in the art.

According to one aspect, the present disclosure provides a method of treating or ameliorating the effects of a skin disease of a mammal in need thereof comprising, providing onto a surface of the skin of the mammal a microbe genetically modified to express one or more LEKTI protein domains, wherein the LEKTI protein domains are effective to penetrate one or more layers of the mammal's skin and effective to inhibit activity of at least one serine protease in or on the mammal's skin. According to some embodiments, the microbe is adapted to live for a controlled duration on the surface of the mammal's skin and to provide a continuous supply of LEKTI protein domains.

According to another aspect, the present disclosure provides a kit for the treatment or amelioration of the effects of a skin disease of a mammal in need thereof comprising: (1)

a composition comprising a microbe that is genetically modified to express one or more LEKTI protein domains, wherein the LEKTI protein domains are effective to penetrate one or more layers of the mammal's skin and effective to inhibit serine protease activity of at least one serine protease in or on the mammal's skin; and (2) reagents for applying the composition to the skin of the mammal. According to some embodiments, the microbes are adapted to live for a controlled duration on the surface of the mammal's skin and to provide a continuous supply of LEKTI protein domains.

In addition to the above components, the subject kits will further include instructions for use of the components and/or practicing the subject methods. These instructions may be present in the subject kits in a variety of forms, one or more of which may be present in the kit. One form in which these instructions may be present is as printed information on a suitable medium or substrate, such as a piece or pieces of paper on which the information is printed, in the packaging of the kit, or in a package insert. Yet another means would be a computer readable medium, such as diskette, or CD, on which the information has been recorded. Further, another means by which the instructions may be present is a website address used via the internet to access the information at a removed site. Any convenient means may be present in the kits.

The components of the kits may be packaged either in aqueous media or in lyophilized form. The kits will generally be packaged to include at least one vial, test tube, flask, bottle, syringe or other container means, into which the described reagents may be placed, and preferably, suitably aliquoted. Where additional components are provided, the kit will also generally contain a second, third or other additional container into which such component may be placed.

The kits of the present disclosure will also typically include a means for containing the reagent containers in close confinement for commercial sale. Such containers may include injection or blow-molded plastic containers into which the desired vials are retained.

Formulations

According to some embodiments the formulation for use according to the present invention can comprise any pharmaceutically effective amount of the recombinant bacteria to produce a therapeutically effective amount of the desired polypeptide or therapeutically effective domain(s) thereof, for example, at least about 0.01%, about 0.05%, about 0.1%, about 0.2%, about 0.3%, about 0.4%, about 0.5%, about 0.6%, about 0.7%, about 0.8%, about 0.9%, about 1.0%, about. 1.5%, about 2.0%, about 3.0%, about 4.0%, about 5.0%, about 6.0%, about 7.0%, about 8.0%, about 9.0%, about 10.0%, about 11.0%, about 12.0%, about 13.0%, about 14.0%, about 15.0%, about 16.0%, about 17.0%, about 18.0%, about 19.0%, about 20.0%, about 25.0%, about 30.0%, about 35.0%, about 40.0%, about 45.0%, about 50.0% or more by weight of recombinant bacteria, the upper limit of which is about 90.0% by weight of recombinant, bacteria.

According to some embodiments, the formulation for use according to the present invention can comprise, for example, at least about 0.01% to about 30%, about 0.01% to about 20%, about 0.01% to about 5%, about 0.1% to about 30%, about 0.1% to about 20%, about 0.1% to about 15%, about 0.1% to about 10%, about 0.1% to about 5%, about 0.2% to about 5%, about 0.3% to about 5%, about 0.4% to about 5%, about 0.5% to about 5%, about 1% to about 5%, or more by weight of recombinant bacteria.

According to some embodiments, the topical formulation can be in any form suitable for application to the body surface, such as a cream, lotion, sprays, solution, gel, ointment, paste, plaster, paint, bioadhesive, suspensions, emulsions, or the like, and/or can be prepared so as to contain liposomes, micelles, and/or microspheres. Such a formulation can be used in combination with an occlusive overlayer so that moisture evaporating from the body surface is maintained within the formulation upon application to the body surface and thereafter. According to some embodiments, the formulation can include a living cell culture composition and can comprise at least one engineered bacterial strain that produces a therapeutically effective recombinant polypeptide or therapeutically effective domain(s) thereof. This engineered living cell culture composition can deliver the polypeptide directly to the skin for treating or preventing abnormal skin conditions.

Topical formulations include those in which any other active ingredient(s) is (are) dissolved or dispersed in a dermatological vehicle known in the art (e.g. aqueous or nonaqueous gels, ointments, water-in-oil or oil-in-water emulsions). Constituents of such vehicles can comprise water, aqueous buffer solutions, non-aqueous solvents (such as ethanol, isopropanol, benzyl alcohol, 2-(2-ethoxyethoxy) ethanol, propylene glycol, propylene glycol monolaurate, glycofurol or glycerol), oils (e.g. a mineral oil such as a liquid paraffin, natural or synthetic triglycerides such as Miglyol™, or silicone oils such as dimethicone). Depending, inter alia, upon the nature of the formulation as well as its intended use and site of application, the dermatological vehicle employed can contain one or more components (for example, when the formulation is an aqueous gel, components in addition to water) selected from the following list: a solubilizing agent or solvent (e.g. a β-cyclodextrin, such as bydroxypropyl β-cyclodextrin, or an alcohol or polyol such as ethanol, propylene glycol or glycerol); a thickening agent (e.g. hydroxyethylceliulose, hydroxypropylcellulose, carboxymethylcellulose or carbomer); a gelling agent (e.g. a polyoxyethylene-polyoxypropylene copolymer); a preservative (e.g. benzyl alcohol, benzalkonium chloride, chlorhexidine, chlorbutol, a benzoate, potassium sorbate or EDTA or salt thereof); and pH buffering agent(s) (such as a mixture of dihydrogen phosphate and hydrogen phosphate salts, or a mixture of citric acid and a hydrogen phosphate salt).

A pharmaceutically acceptable carrier can also be incorporated in the formulation of the present invention and can be any carrier conventionally used in the art. Examples thereof include water, lower alcohols, higher alcohols, polyhydric alcohols, monosaccharides, disaccharides, polysaccharides, hydrocarbon oils, fats and oils, waxes, fatty acids, silicone oils, nonionic surfactants, ionic surfactants, silicone surfactants, and water-based mixtures and emulsion-based mixtures of such carriers. The term "pharmaceutically acceptable" or "pharmaceutically acceptable carrier" is used herein to refer to a compound or composition that can be incorporated into a pharmaceutical formulation without causing undesirable biological effects or unwanted, interaction with other components of the formulation, "Carriers" or "vehicles" as used herein refer to carrier materials suitable for incorporation in a topically applied composition. Carriers and vehicles useful herein include any such materials known in the art, which are non-toxic and do not interact with other components of the formulation in which it is contained in a deleterious manner. The term "aqueous" refers to a formulation that contains water or that becomes water-containing following application to the skin or mucosal tissue.

A film former, when it dries, forms a protective film over the site of application. The film inhibits removal of the active ingredient and keeps it in contact with the site being treated. An example of a film former that is suitable for use in this invention is Flexible Collodion, US P. As described in Remington: The Science and Practice of Pharmacy, 19th Ed. (Easton, PA: Mack Publishing Co., 1995), at page 1530, collodions are ethyl ether/ethanol solutions containing pyroxylin (a nitrocellulose) that evaporate to leave a film of pyroxylin. A film former can act additionally as a carrier. Solutions that dry to form a film are sometimes referred to as paints. Creams, as is well known in the arts of pharmaceutical formulation, are viscous liquids or semisolid emulsions, either oil-in-water or water-in-oil.

Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

Lotions are preparations to be applied to the skin surface without friction, and are typically liquid or semiliquid preparations in which particles, including the active agent, are present in a water or alcohol base. Lotions are usually suspensions of solids, and preferably, comprise a liquid oily emulsion of the oil-in-water type. Lotions are preferred formulations herein for treating large body areas, because of the case of applying a more fluid composition. It is generally necessary that the insoluble matter in a lotion be finely-divided.

Lotions will typically contain suspending agents to produce better dispersions as well as compounds useful for localizing and holding the active agent in contact with the skin, e.g., methylcellulose, sodium carboxymethyl-cellulose, or the like.

Solutions are homogeneous mixtures prepared by dissolving one or more chemical substances (solutes) in a liquid such that the molecules of the dissolved substance are dispersed among those of the solvent. The solution can contain other pharmaceutically or cosmetically acceptable chemicals to buffer, stabilize or preserve the solute. Common examples of solvents used in preparing solutions are ethanol, water, propylene glycol or any other acceptable vehicles. As is of course well known, gels are semisolid, suspension-type systems. Single-phase gels contain organic macromolecules distributed substantially uniformly throughout the carrier liquid, which is typically aqueous, but also, preferably, contain an alcohol, and, optionally, an oil. Preferred "organic macromolecules," i.e., gelling agents, are cross-linked acrylic acid polymers such as the "carbomer" family of polymers, e.g., carboxypolyalkylenes that can be obtained commercially under the Carbopol trademark. Also preferred are hydrophilic polymers such as polyethylene oxides, polyoxyethylene-polyoxypropylene copolymers and polyvinylalcohol; cellulosic polymers such as hydroxy-propyl cellulose, hydroxyethyl cellulose, hydroxypropyl methylcellulose, hydroxy-propyl methylcellulose phthaiate, and methylcellulose; gums such as tragacanth and xanthan gum; sodium alginate; and gelatin, In order to prepare a uniform gel, dispersing agents such as alcohol or glycerin can be added, or the gelling agent can be dispersed by trituration, mechanical mixing or stirring, or combinations thereof. Ointments, as also well known in the art, are semisolid preparations that are typically based on petrolatum or other petroleum derivatives. The specific ointment base to be used, as will be appreciated by those skilled in the art, is one that will provide for a number of desirable characteristics, e.g., emolliency or the like. As with other carriers or vehicles, an ointment base should be inert, stable, nonirritating, and nonsensitizing. As explained in Remington: The Science and Practice of Pharmacy, 19th Ed. (Easton, PA: Mack Publishing Co., 1995), at pages 1399-1404, ointment bases can be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum.

Emulsifiable ointment bases, also known as absorbent ointment bases, contain little or no water and include, for example, hydroxystearin sulfate, anhydrous lanolin, and hydrophilic petrolatum.

Emulsion ointment bases are either water-in-oil (W/O) emulsions or oil-in-water (O/W) emulsions, and include, for example, acetyl alcohol, glyceryl monostearate, lanolin, and stearic acid. Preferred water-soluble ointment bases are prepared from polyethylene glycols of varying molecular weight; see Remington: The Science and Practice of Pharmacy for further information.

Pastes are semisolid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

Enhancers are those lipophilic co-enhancers typically referred to as "plasticizing" enhancers, i.e., enhancers that have a molecular weight in the range of about 150 to 1000, an aqueous solubility of less than about 1 wt. %, preferably less than about 0.5 wt. %, and most preferably less than about 0.2 wt. %. The Hildebrand solubility parameter $\delta$ of plasticizing enhancers is in the range of about 2.5 to about 10, preferably in the range of about 5 to about 10. Preferred lipophilic enhancers are fatty esters, fatty alcohols, and fatty ethers. Examples of specific and most preferred fatty acid esters include methyl laurate, ethyl oleate, propylene glycol nionolaurace, propylene glycerol dilaurate, glycerol mono-laurate, glycerol monooleate, isopropyl n-decanoate, and octyldodecyl myristate. Fatty alcohols include, for example, stearyl alcohol and oleyl alcohol, while fatty ethers include compounds wherein a diol or triol, preferably a $C_2$-$C_4$ alkane diol or triol, are substituted with one or two fatty ether substituents.

Additional permeation enhancers will be known to those of ordinary skill in the art of topical drug delivery, and/or are described in the pertinent texts and literature. See, e.g., Percutaneous Penetration Enhancers, eds. Smith et al. (CRC Press, 1995)(incorporated herein by reference).

Various other additives can be included in the compositions of the present invention in addition to those identified above. These include, but are not limited to, antioxidants, astringents, perfumes, preservatives, emollients, pigments, dyes, humectants, propeliants, and sunscreen agents, as well as other classes of materials whose presence can be pharmaceutically or otherwise desirable. Typical examples of optional additives for inclusion in the formulations of the invention are as follows: preservatives such as sorbate; solvents such as isopropanol and propylene glycol; astringents such as menthol and ethanol; emollients such as polyalkylene methyl glucosides; humectants such as glycerine; emulsifiers such as glycerol stearate, PEG-100 stearate, polyglyceryl-3 hydroxylauryl ether, and polysorbate 60; sorbitol and other polyhydroxyalcohols such as polyethylene glycol; sunscreen agents such as octyl methoxyl cinnamate (available commercially as Parsol MCX) and butyl methoxy benzoylmethane (available under the tradename Parsol 1789); antioxidants such as ascorbic acid (vitamin C), a-tocopherol (Vitamin E), $\beta$-tocopherol, $\gamma$-tocopherol, $\delta$-tocopherol, $\epsilon$-tocopherol, $\zeta_1$-tocopherol, $Z^\Lambda$-tocopherol, $\eta$-tocopherol, and retinol (vitamin A); essential oils, ceramides, essential fatty acids, mineral oils, vegetable oils (e.g., soya bean oil, palm oil, liquid fraction of shea butter, sunflower oil), animal oils (e.g., perhydrosqualene), synthetic oils, silicone oils or waxes (e.g., cyclomethicone and dimethicone), fluorinated oils (generally perfluoropolyethers), fatty alcohols (e.g., cetyl alcohol), and waxes (e.g., beeswax, carnauba wax, and paraffin wax); skin-feel modifiers; and thickeners and structurants such as swelling clays and cross-linked carboxypolyalkylenes that can be obtained commercially under the Carbopol trademark. Other additives include beneficial agents such as those materials that condition the skin (particularly, the upper layers of the skin in the stratum corneum) and keep it soft by retarding the decrease of its water content and/or protect the skin. Such conditioners and moisturizing agents include, by way of example, pyrrolidine carboxylic acid and amino acids; organic antimicrobial agents such as 2,4,4'-trichloro-2-hydroxy diphenyl ether (triclosan) and benzoic acid; anti-inflammatory agents such as acetylsalicylic acid and glycyrrhetinic acid; anti-seborrhoeic agents such as retinoic acid; vasodilators such as nicotinic acid; inhibitors of melanogenesis such as kojic acid; and mixtures thereof. Further additional active agents including, for example, alpha hydroxyacids, alpha ketoacids, polymeric hydroxyacids, moisturizers, collagen, marine extract, and antioxidants such as ascorbic acid (Vitamin C), a-tocopherol (Vitamin E), $\beta$-tocopherol, $\gamma$-tocopherol, 6-tocopherol, $\epsilon$-tocopherol, $\zeta_1$-tocopherol, $\zeta_2$-tocopherol, $\eta$-tocopherol, and retinol (Vitamin A), and/or pharmaceutically acceptable salts, esters, amides, or other derivatives thereof. A preferred tocopherol compound is a-tocopherol. Additional agents include those that are capable of improving oxygen supply in skin tissue, as described, for example, in Gross, et al, WO 94/00098 and Gross, et al, WO 94/00109, both assigned to Lancaster Group AG (incorporated herein by reference). Sunscreens and UV absorbing compounds can also be included. Non-limiting examples of such sunscreens and UV absorbing compounds include aminobenzoic acid (PABA), avobenzone, cinoxate, dioxybenzone, homosalate, menthyl anthranilate, oxtocrylene, octyl methoxycmnamate, octyl salicylate, oxybenzone, padirnate O, phenylbenzirmdazole sulfonic acid, sulisobenzone, titanium dioxide, trolamine salicylate, zinc oxide, ensulizole, meradiraate, octinoxate, octisalate, and octocrylene. See Title 21. Chapter 1. Subchapter D. Part 352. "Sunscreen drug products for over-the-counter human use" incorporated herein in its entirety.

Other embodiments can include a variety of non-carcinogenic, non-irritating healing materials that facilitate treatment with the formulations of the invention. Such healing materials can include nutrients, minerals, vitamins, electrolytes, enzymes, herbs, plant extracts, glandular or animal extracts, or safe therapeutic agents that can be added to the formulation to facilitate the healing of dermal disorders.

The amounts of these various additives are those conventionally used in the cosmetics field, and range, for example, from about 0.01% to about 20% of the total weight of the topical formulation.

The formulations of the invention can also include conventional additives such as opacifiers, fragrance, colorant, stabilizers, surfactants, and the like. In certain embodiments, other agents can also be added, such as antimicrobial agents, to prevent spoilage upon storage, i.e., to inhibit growth of microbes such as yeasts and molds.

Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof. In other embodiments, other agents can also be added, such as repressors and inducers, i.e., to inhibit (i.e. glycose) or induce (i.e. xylose) the production of the polypeptide of interest. Such additives can be employed provided they are compatible with and do not interfere with the function of the formulations.

The formulations can also contain irritation-mitigating additives to minimize or eliminate the possibility of skin irritation or skin damage resulting from the chemical entity to be administered, or other components of the composition. Suitable irritation-mitigating additives include, for example: a-tocopherol; monoamine oxidase inhibitors, particularly phenyl alcohols such as 2-phenyl-1-ethanol; glycerin; salicylates; ascorbates; ionophores such as monensin; amphophilic amines; ammonium chloride; N-acetylcysteine; capsaicin; and chloroquine. The irritation-mitigating additive, if present, can be incorporated into the composition at a concentration effective to mitigate irritation or skin damage, typically representing not more than about 20 wt. %, more typically not more than about 5 wt. %, of the formulation.

Further suitable pharmacologically active agents that can be incorporated into the present formulations in certain embodiments and thus topically applied along with the active agent include, but are not limited to, the following: agents that improve or eradicate pigmented or non-pigmented age spots, keratoses, and wrinkles; antimicrobial agents; antibacterial agents; antipruritic and antixerotic agents; anti-inflammatory agents; local anesthetics and analgesics; corticosteroids; retinoids; vitamins; hormones; and antimetabolites.

Some examples of topical pharmacologically active agents include acyclovir, amphotericins, chlorhexidine, clotrimazole, ketoconazole, econazole, miconazole, metronidazole, minocycline, nystatin, neomycin, kanamycin, phenytoin, para-amino benzoic acid esters, octyl methoxycmnamate, octyl salicylate, oxybenzone, dioxybenzone, tocopherol, tocopheryl acetate, selenium sulfide, zinc pyrithione, diphenhydramine, pramoxine, lidocaine, procaine, erythromycin, tetracycline, clindamycin, crotamiton, hydroquinone and its monomethyl and benzyl ethers, naproxen, ibuprofen, cromolyn, retinol, retinyl palmitate, retinyl acetate, coal tar, griseofulvin, estradiol, hydrocortisone, hydrocortisone 21-acetate, hydrocortisone 17-valerate, hydrocortisone 17-butyrate, progesterone, betamethasone valerate, betamethasone dipropionate, triamcinolone acetonide, fluocinonide, clobetasol propionate, minoxidil, dipyridamole, diphenylhydantoin, benzoyl peroxide, and 5-fluorouracil.

A cream, lotion, gel, ointment, paste or the like can be spread on the affected surface and gently rubbed in. A solution can be applied in the same way, but more typically will be applied with a dropper, swab, or the like, and carefully applied to the affected areas.

The application regimen will depend on a number of factors that can readily be determined, such as the severity of the condition and its responsiveness to initial treatment, but will normally involve one or more applications per day on an ongoing basis. One of ordinary skill can readily determine the optimum amount of the formulation to be administered, administration methodologies and repetition rates. In general, it is contemplated that the formulations of the invention will be applied in the range of once or twice weekly up to once or twice daily.

The pharmaceutical compositions of the invention comprise one or more active ingredients, e.g. therapeutic agents, in admixture with one or more pharmaceutically-acceptable diluents or carriers and, optionally, one or more other compounds, drugs, ingredients and/or materials. Regardless of the route of administration selected, the agents/compounds of the present invention are formulated into pharmaceutically-acceptable dosage forms by conventional methods known to those of skill in the art. See, e.g., Remington, The Science and Practice of Pharmacy (21st Edition, Lippincott Williams and Wilkins, Philadelphia, Pa.).

Pharmaceutically acceptable diluents or carriers are well known in the art (sec, e.g., Remington, The Science and Practice of Pharmacy (21st Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable diluent or carrier used in a pharmaceutical composition of the invention must be "acceptable" in the sense of being compatible with the other ingredients of the formulation and not injurious to the subject. Diluents or carriers suitable for a selected dosage form and intended route of administration are well known in the art, and acceptable diluents or carriers for a chosen dosage form and method of administration can be determined using ordinary skill in the art.

The pharmaceutical compositions of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable diluent or carrier. The ointments, pastes, creams and gels may contain excipients. Powders and sprays may contain excipients and propellants.

The pharmaceutical compositions of the present invention suitable for parenteral administrations may comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These pharmaceutical compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

The following examples are provided to further illustrate the methods of the present invention. These examples are illustrative only and are not intended to limit the scope of the invention in any way.

Example 1

Bacteria

In some embodiments, bacteria of the *Staphylococcus aureus* RN4220 strain may be used in preparation of the vector (Kreiswirth, B N et al. 1983). In some such embodiments, a stock solution of the strain is stored at −20° C. in 50% glycerol in LB or TS broth.

According to some embodiments, bacteria of the *Staphylococcus epidermidis* strain ATCC 12228 or NRRL B-4268 may be used (Zhang, Y Q., et ah 2003). In some such embodiments, a stock solution of the strain is stored at −20° C. in 50% glycerol in LB broth or TS broth. Bacteria are cultured in LB broth or TS broth. After 16 hours of incubation, bacteria are harvested by centrifugation and 10-fold concentrated in LB broth or TS broth at $2 \times 10^9$ bacteria/100 ul. A stock preparation of the bacteria is prepared by inoculating 5 mL broth with *S. epidermidis* and grown overnight at 30° C. Then, 3 mL fully grown culture is added to 1 ml 60% glycerol and stored at −80° C.

Expression Vector

According to some embodiments, plasmid construct pKK30-LEKTI-complete may comprise the pKK30 vector with a LEKTI domain insert. According to some embodiments, the LEKTI domain may be operably linked to a SecA secretion signal, a 6×His tag, and/or an RMR cell permeation sequence, with expression under the control of a chloramphenicol-resistance (CmR) promoter sequence (from pDB114E). In some embodiments, the pKK30 vector comprises a dihydrofolate reductase (dfrA) selection gene.

Transformation

According to some embodiments, a vector harboring the LEKTI sequence may be transformed into the *S. epidermidis* strain. The vector harboring the LEKTI sequence may be prepared/transformed comprising the steps of: preparation of competent *S. aureus* bacterial cells, transformation of *S. aureus*, isolation of plasmid DNA from *S. aureus*, preparation of competent *S. epidermidis* bacterial cells, transformation of *S. epidermidis*, growth of transformed *S. epidermidis* bacteria, and storage of transformed *S. epidermidis*.

In some embodiments, alternative intermediate strains can also be used for transformation and isolation of plasmid DNA in preparation for transformation into *S. epidermidis*. These strains may include but are not limited to *E. coli* strains among other bacteria, including those deficient in methylation.

According to some embodiments, *S. aureus* RN4220 cells may be made electrocompetent by growing 50 ml culture overnight in LB or TS medium at 37° C., then inoculating 100 ml fresh LB or TS medium with 10 ml of overnight culture. When $OD_{600}$ reaches 0.2-0.3, cells are pelleted and resuspended with 1× volume of 4° C. 10% sucrose. This process is repeated 3×, and then the cells are resuspended with 0.1× volume of 4° C. 10% sucrose, pelleted, and resuspended with 1 ml of 10% sucrose.

For transformation of RN4220, 200-500 ug of LEKTI plasmid (e.g. pKK30-LEKTI-complete) may be mixed with electrocompetent cells and transformed using electroporation at room temperature at 2.5 kV using the MicroPulser Electroporator (Bio-Rad, Hercules, CA). Transformed cells are plated at 28° C. overnight on selective LB or TB medium, grown overnight in selective LB or TB medium and then used to isolate DNA.

According to some embodiments, electrocompetent *S. epidermidis* ATCC 12228 or NRRL B-4268 are made using the following methods. First, 50 ml overnight culture of ATCC 12228 or NRRL B-4268 from a −80° C. stock are grown at 37° C. in B2 medium (1.0% tryptone, 2.5% yeast extract, 0.5% glucose, 2.5% NaCl, 0.1% $K_2PO_4$, pH to 7.5). 10 ml of overnight culture is diluted into fresh pre-warmed B2 media and shaken until $OD_{600}$ reaches 0.5-0.6 and then pelleted for 10 min at 4° C. Next, cells are washed with 1, ½, ¹⁄₂₀, and ¹⁄₅₀ volumes of cold 10% glycerol, pelleting at 4° C. between washes. The final pellet is resuspended in 700 ul of cold 10% glycerol.

According to some embodiments, electrocompetent ATCC 12228 or NRRL B-4268 are transformed with pKK30-LEKTI-complete, isolated from *S. aureus*, using electroporation at 2.5 kV, 25 uF, 100Ω. (normal reading is 4.5-5 msec using the Micropulser Electroporator (Bio-Rad, Hercules, CA)). Cells are then plated at 28° C. on selective LB or TB medium. In some embodiments, transformation of the bacteria can also be performed via alternative methods of transformation including but not limited to alternative intermediate strains, bacteriophage transduction, and heat shock.

Analysis of Protein Expression

According to some embodiments, transformed cells are fractionated and analyzed via SDS-PAGE electrophoresis and western blotting. Bacterial cells expressing recombinant LEKTI and bacterial control cells are pelleted and lysed with CelLytic B Cell Lysis Reagent (Sigma-Aldrich, St. Louis, MO). The supernatant from the induced sample is collected and concentrated. Samples are resuspended in a reduced sample buffer and then electrophoresed on a 4-15% Tris-acrylimide gel with Tris-HCL running buffer. Following electrophoresis, the gel is transferred to a PVDF membrane, and sequentially probed with a primary goat monoclonal antibody against LEKTI domains 8-11 or a His tag. A horseradish peroxidase-conjugated donkey anti-goat antibody (sc-2020) is then probed and the secondary antibodies detected through autoradiography (Syngene GeneGnome Bio Imaging System) using enhanced chemiluminescence substrate (SuperSignal West Pico, Thermo Scientific).

Analysis of the supernatant and cell lysate demonstrates the successful expression and secretion of the therapeutic polypeptide upon transformation with a plasmid containing the protein of interest. Detection of protein expression and secretion is also possible using alternative methods and the current example should not be construed as a limitation to the present invention.

Treatment of Human Subjects

According to some embodiments, $1 \times 10^9$ colony forming units (CFU) of *S. epidermidis* containing recombinant LEKTI can be added to a pharmaceutically acceptable carrier. The foregoing composition is useful for treating or preventing abnormal skin conditions resulting from Netherton Syndrome in a subject in need thereof. The composition can be applied at least once per day, up to for example about 3 to 4 times per day, or as needed or prescribed. In some embodiments, only a single application is required to achieve a therapeutic effect. The composition can be used for as long as needed to ensure treatment of the condition or to continue to prevent the condition. The duration of treatment can vary from about 1 day up to about 10 to 14 days or longer. In certain instances, long term or chronic treatment can be administered.

Example 2

Testing Serine Protease Inhibition Activity of Recombinant LEKTI

According to some embodiments, the protease inhibition activity of recombinant LEKTI is tested for differences achieved when operably linked to various secretion peptides and cell penetration peptides. According to some embodiments, specific combinations of secretion peptides and cell penetration peptides may have unpredictable effects on the protease inhibition function of the LEKTI domains, and therefore may be determined empirically.

In some embodiments, LEKTI domains D8-D11, operably linked to a secretory tag, 6×His tag, and/or cell penetration tag, are cloned into an insect expression vector for large scale production of purified recombinant protein and assessed for inhibitory activity on one or more proteases (e.g. plasmin, cathepsin G, elastase, and trypsin).

Insect Cells and Reagents

The following reagents may be obtained commercially as indicated: Fall Army worm cell line *Spodoptera frugiperda* (Sf9), low-melting point agarose, cellFECTIN, pFAST-BAC1, pCRII-TOPO, *Escherichia* colicompetent DH10BAC, cabbage looper egg cell line *Trichoplusia ni* 5B1-4 (High Five), and ultimate serum-free insect medium from Invitrogen (Carlsbad, CA); restriction endonucleases from New England Biolabs (Beverly, MA); TALON Superflow from Clontech Laboratory (Palo Alto, CA); Insect-XPRESS medium and fetal bovine serum from BioWhittaker (Walkersville, MD); YM10 Centriplus from Millipore Corp. (Bedford, MA); precast SDS-PAGE gels, protein assay kit, SEC-250 size column, and prestained markers from Bio-Rad (Hercules, CA); BSA from Kabi Pharmacia (Franklin, OH); DTT and glycerol from Bochringer Mannheim Biochemicals (Indianapolis, IN); and penta-His mAb and six-His tagged protein ladder from QIAGEN Inc. (Valencia, CA).

Cloning and Expression of LEKTI D8-D11

6×His tagged LEKTI domains (e.g. SEQ ID NO: 1) operably linked to various permutations of secretion peptides and cell penetration peptides may be cloned into the pFASTBAC1 vector according to the manufacturers' instructions. Recombinant LEKTI composite viruses are then generated as previously described by Gao, M. et al., (1996) J. Biol. Chem. 271, 27782-27787, which is incorporated herein by reference in its entirety. To test the recombinant LEKTI composite viruses for recombinant LEKTI expression, Sf9 cells may be infected at varying multiplicities of infection with recombinant viruses, and the cell lysate and medium collected every 24-96 h. The presence of histidine-tagged protein may be confirmed by Western blot analysis using penta-His mAb directed against the six-histidine tag as per the manufacturer's recommendations. LEKTI composite viruses that displayed the highest level of expression may be chosen for further experiments and spinner flasks.

The recombinant LEKTI protein may be produced on a large scale by infecting spinner cultures of Sf9 cells (1.6 billion cells) in 10% serum containing Insect-XPRESS medium at a multiplicity of infection of 8 plaque forming units (PFU). Three days after infection, the cell pellet may be harvested and the recombinant LEKTI selectively purified from the cell lysate using a $Co^{2+}$-charged Sepharose affinity column (TALON) followed by SEC-250 size column chromatography, as previously described in Jayakumar, A. et al., (1995) Proc. Natl. Acad. Sci. U.S.A. 92, 8695-8699. Fractions containing homogeneous LEKTI may be pooled and concentrated by ultrafiltration. Protein may be quantified using the Bio-Rad Protein Assay Kit II.

Protease Inhibition Assay Reagents and Protocol

The following enzymes, chromogenic substrates, and reagents may be obtained commercially as indicated: human plasmin, human cathepsin L, human cathepsin S, human trypsin, human cathepsin G, human chymotrypsin, and human neutrophil elastase (HNE) from Athens Research & Technology, Inc. (Athens, GA); subtilisin A from Calbiochem-Novabiochem (San Diego, CA); papain from Roche Molecular Biochemicals (Indianapolis, IN); furin from New England BioLabs; succinyl-Ala-Ala-Pro-Phe-p-nitroanilide (Succ-AAPF-pNA), succinyl-Ala-Ala-Val-pNA (Succ-AAVpNA), andD-Val-Leu-Lys-pNA (VLK-pNA) from Sigma Chemical Co. (St. Louis, MO); H-Glu-Gly-Arg-pNA (EGRpNA) and benzyloxycarbonyl-Phe-Arg-pNA (Z-FR-pNA) from Bachem Bioscience, Inc. (King of Prussia, PA); and methoxy-Succ-Arg-Pro-Tyr-pNA (MeO-Succ-RPY-pNA) from Chromogenix Instrumentation Laboratory SpA (Milan, Italy). PBS reaction buffer (137 mM NaCl, 27 mM KCl, and 10 mM phosphate buffer (pH 7.4)) may be used with trypsin, plasmin, cathepsin G, HNE, and chymotrypsin. Cathepsin reaction buffer (0.1% CHAPS, 50 mM sodium acetate (pH 5.5), 1 mM EDTA) may be used with cathepsins K, L, and S and papain. A unique reaction buffer may be used with subtilisin A (PBS and 0.1% Tween 20).

Proteinase inhibitory activity may be detected by the ability of recombinant LEKTI to block the cleavage of small, chromogenic peptide substrates as determined by a spectroscopy technique described previously in Schick, C. et al., (1998) Biochemistry 37, 5258-5266, which is incorporated herein by reference in its entirety. Inhibition of proteinase may be assessed after preincubating the enzyme with recombinant LEKTI for 2 min at 25° C. in 100 uL of assay buffer. This mixture may be added to 890 or 880 uL of assay buffer in a 1 mL quartz cuvette. The proteinase activity may be initiated by adding 10-20 uL of the appropriate pNA substrate. The change in absorbance at 405 nm ($A_{405}$=8.8 $10^{-3}$ $M^{-1}$ $cm^{-1}$) may be followed for as long as 10 min using a spectrophotometer (Beckman Instruments, Inc., Fullerton, CA). The rate changes ($\Delta A_{405}$/min) of inhibited and control reactions may be determined from velocity plots.

According to some embodiments, different combinations of secretory tag and cell penetration tag may cause differing LEKTI protease activity on each of the tested proteases (e.g. trypsin, plasmin, cathepsin G, HNE, subtilisin A, and chymotrypsin). Furthermore, discrete combinations of secretory tag and cell penetration tag may cause differing LEKTI protease activity among individual proteases.

Example 3

Penetrating Peptide Mediated Delivery

According to some embodiments, various combinations of secretory tag and cell penetration tag may affect the ability of the recombinant LEKTI protein to pass through a cell membrane to a greater or lesser degree. Thus, the various recombinant LEKTI products may be tested in cell culture to assess the effect of the various combinations of secretory tag and cell penetration tag.

According to some embodiments, adherent fibroblastic HS-68, NIH-3T3, 293, Jurkat T, or Cos-7 cell lines may be cultured in Dulbecco's modified Eagle's medium (DMEM) supplemented with 1% (vol/vol) 200 mM glutamine, 1% (vol/vol) antibiotics (streptomycin, 10,000 µg/ml; penicillin, 10,000 IU/ml), and 10% (wt/vol) FBS, at 37° C. in a humidified atmosphere containing 5% CO2. For peptide-mediated delivery of recombinant LEKTI proteins, purified recombinant LEKTI product (as obtained above) may be loaded in DMEM or PBS (500 µl of DMEM containing 0.25 µg of protein) and incubated for 30 min at 37° C. Cells grown to 75% confluency are then overlaid with these recombinant LEKTI protein media. After 30 min incubation at 37° C., 1 ml of fresh DMEM supplemented with 10% FBS is added to the cells, without removing the overlay of recombinant LEKTI protein, and cells are returned to the incubator for another 30 min. Cells are then extensively washed with PBS and examined for recombinant LEKTI protein. Cells could be observed by immunofluorescence by first fixing with 2% formalin (Sigma), permeabilizing, then incubating with primary anti-6×His tag antibody and secondary antibody according to the manufacturers' instruction. Alternatively cells lysates could be obtained and the presence of His tagged recombinant LEKTI observed via Western blot, as described above.

According to some embodiments, certain combinations of secretory protein and penetrating peptide have differing effects on the ability of the recombinant LEKTI protein's ability to pass through the cell membrane.

Example 4

Figure 3:
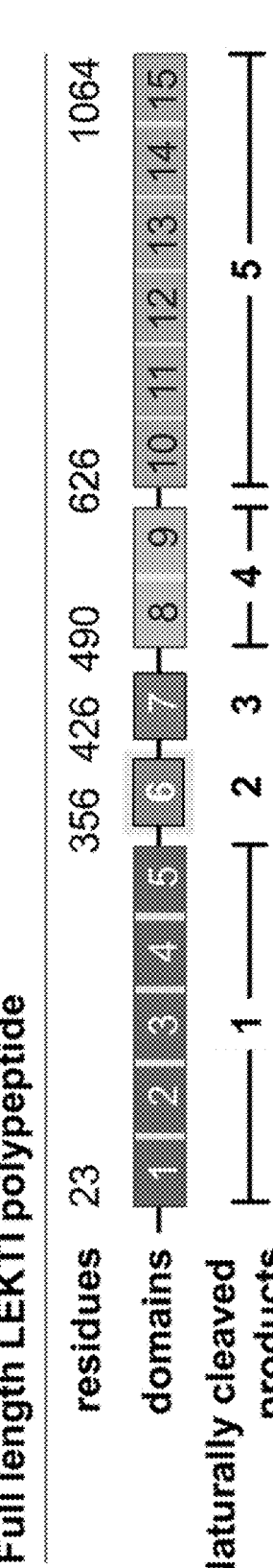
FIG. 3 is a schematic showing the domains of the full length LEKTI polypeptide.

The LEKTI protein requires proteolytic cleavage for activation of its inhibitory function against many proteases. The full length protein is cleaved into domains D1-D5 and D6-D15. The D6-D15 domains are then further cleaved in multiple steps into D6-D9 and D10-D15, →D6 and D7-D9→D7 and D8-D9→D8. A schematic of the full-length LETKI polypeptides, the domains and the naturally cleaved products is shown in FIG. 3. In selecting a particular domain to express, the following criteria of the domain were considered: (1) active on various kallikrein-related peptidases (KLK) such as KLK5 and KLK7; (2) protease resistant; (3) small (not a metabolic burden); (4) contains minimal disulfide bond content. Domain 6 was selected as a LETKI fragment to express. The amino acid sequence of full length LEKTI protein is set forth as SEQ ID NO:103. as well as each of the 15 individual domains below in fasta format:

```
LEKTI amino acid sequence Residues 1-1064
(SEQ ID NO: 103):
MKIATVSVLLPLALCLIQDAASKNEDQEMCHEFQAFMKNGKLFCPQDKKF

FQSLDGIMFINKCATCKMILEKEAKSQKRARHLARAPKATAPTELNCDDF

KKGERDGDFICPDYYEAVCGTDGKTYDNRCALCAENAKTGSQIGVKSEGE

CKSSNPEQDVCSAFRPFVRDGRLGCTRENDPVLGPDGKTHGNKCAMCAEL

FLKEAENAKREGETRIRRNAEKDFCKEYEKQVRNGRLFCTRESDPVRGPD

GRMHGNKCALCAEIFKQRFSEENSKTDQNLGKAEEKTKVKREIVKLCSQY

QNQAKNGILFCTRENDPIRGPDGKMHGNLCSMCQAYFQAENEEKKKAEAR

ARNKRESGKATSYAELCSEYRKLVRNGKLACTRENDPIQGPDGKVHGNTC

SMCEVFFQAEEEEKKKKEGKSRNKRQSKSTASFEELCSEYRKSRKNGRLF

CTRENDPIQGPDGKMHGNTCSMCEAFFQQEERARAKAKREAAKEICSEFR

DQVRNGTLICTREHNPVRGPDGKMHGNKCAMCASVFKLEEEEKKNDKEEK

GKVEAEKVKREAVQELCSEYRHYVRNGRLPCTRENDPIEGLDGKIHGNTC

SMCEAFFQQEAKEKERAEPRAKVKREAEKETCDEFRRLLQNGKLFCTREN
```

```
-continued
DPVRGPDGKTHGNKCAMCKAVFQKENEERKRKEEEDQRNAAGHGSSGGGG

GNTQDECAEYREQMKNGRLSCTRESDPVRDADGKSYNNQCTMCKAKLERE

AERKNEYSRSRSNGTGSESGKDTCDEFRSQMKNGKLICTRESDPVRGPDG

KTHGNKCTMCKEKLEREAAEKKKKEDEDRSNTGERSNTGERSNDKEDLCR

EFRSMQRNGKLICTRENNPVRGPYGKMHINKCAMCQSIFDREANERKKKD

EEKSSSKPSNNAKDECSEFRNYIRNNELICPRENDPVHGADGKFYTNKCY

MCRAVFLTEALERAKLQEKPSHVRASQEEDSPDSFSSLDSEMCKDYRVLP

RIGYLCPKDLKPVCGDDGQTYNNPCMLCHENLIRQTNTHIRSTGKCEESS

TPGTTAASMPPSDE
```

LEKTI Domains are set forth below:

```
LEKTI Domain 1
                 (residues 23-77; SEQ ID NO: 104)
KNEDQEMCHEFQAFMKNGKLFCPQDKKFFQSLDGIMFINKCATCKMILEK

EAKSQ
```

```
LEKTI Domain 2
                 (residues 91-153; SEQ ID NO: 105)
APTELNCDDFKKGERDGDFICPDYYEAVCGTDGKTYDNRCALCAENAKTG

SQIGVKSEGECKS
```

```
LEKTI Domain 3
                 (residues 155-216; SEQ ID NO: 106)
NPEQDVCSAFRPFVRDGRLGCTRENDPVLGPDGKTHGNKCAMCAELFLKE

AENAKREGETRI
```

```
LEKTI Domain 4
                 (residues 219-285; SEQ ID NO: 107)
NAEKDFCKEYEKQVRNGRLFCTRESDPVRGPDGRMHGNKCALCAEIFKQR

FSEENSKTDQNLGKAEE
```

```
LEKTI_Domain 5
                 (residues 291-352; SEQ ID NO: 108)
REIVKLCSQYQNQAKNGILFCTRENDPIRGPDGKMHGNLCSMCQAYFQAE

NEEKKKAEARAR
```

```
LEKTI_Domain 6
                 (residues 356-423; SEQ ID NO: 109)
ESGKATSYAELCSEYRKLVRNGKLACTRENDPIQGPDGKVHGNTCSMCEV

FFQAEEEEKKKKEGKSRN
```

```
LEKTI Domain 7
                 (residues_431-489; SEQ ID NO: 110)
ASFEELCSEYRKSRKNGRLFCTRENDPIQGPDGKMHGNTCSMCEAFFQQE

ERARAKAKR
```

```
LEKTI Domain 8
                 (residues 490-550; SEQ ID NO: 111)
EAAKEICSEFRDQVRNGTLICTREHNPVRGPDGKMHGNKCAMCASVFKLE

EEEKKNDKEEKG
```

```
LEKTI Domain 9
                 (residues_561_622; SEQ ID NO: 112)
EAVQELCSEYRHYVRNGRLPCTRENDPIEGLDGKIHGNTCSMCEAFFQQE

AKEKERAEPRAK
```

```
LEKTI Domain 10
                 (residues 626-688; SEQ ID NO: 113)
EAEKETCDEFRRLLQNGKLFCTRENDPVRGPDGKTHGNKCAMCKAVFQKE

NEERKRKEEEDQR
```

-continued

LEKTI Domain 11
                    (residues 701-757; SEQ ID NO: 114)
GNTQDECAEYREQMKNGRLSCTRESDPVRDADGKSYNNQCTMCKAKLERE

AERKNEY

LEKTI Domain 12
                    (residues 768-830; SEQ ID NO: 115)
ESGKDTCDEFRSQMKNGKLICTRESDPVRGPDGKTHGNKCTMCKEKLERE

AAEKKKKEDEDRS

LEKTI Domain 13
                    (residues 843-905; SEQ ID NO: 116)
NDKEDLCREFRSMQRNGKLICTRENNPVRGPYGKMHINKCAMCQSIFDRE

ANERKKKDEEKSS

LEKTI Domain 14
                    (residues 910-970; SEQ ID NO: 117)
NNAKDECSEFRNYIRNNELICPRENDPVHGADGKFYTNKCYMCRAVFLTE

ALERAKLQEKPS

LEKTI Domain 15
                    (residues 987-1048; SEQ ID NO: 118)
SLDSEMCKDYRVLPRIGYLCPKDLKPVCGDDGQTYNNPCMLCHENLIRQT

NTHIRSTGKCEE

LEKTI nucleic acid sequence is set forth below as SEQ
ID NO:119.

LETKI Full length Nuceic acid sequence
                               (SEQ ID NO: 119)
ATGAAGATAGCCACAGTGTCAGTGCTTCTGCCCTTGGCTCTTTGCCTCAT

ACAAGATGCTGCCAGTAAGAATGAAGATCAGGAAATGTGCCATGAATTTC

AGGCATTTATGAAAAATGGAAAACTGTTCTGTCCCCAGGATAAGAAATTT

TTTCAAAGTCTTGATGGAATAATGTTCATCAATAAATGTGCCACGTGCAA

AATGATACTGGAAAAAGAAGCAAAATCACAGAAGAGGGCCAGGCATTTAG

CAAGAGCTCCCAAGGCTACTGCCCCAACAGAGCTGAATTGTGATGATTTT

AAAAAAGGAGAAAGAGATGGGGATTTTATCTGTCCTGATTATTATGAAGC

TGTTTGTGGCACAGATGGGAAAACATATGACAACAGATGTGCACTGTGTG

CTGAGAATGCGAAAACCGGGTCCCAAATTGGTGTAAAAAGTGAAGGGGAA

TGTAAGAGCAGTAATCCAGAGCAGGATGTATGCAGTGCTTTTCGGCCCTT

TGTTAGAGATGGAAGACTTGGATGCACAAGGGAAAATGATCCTGTTCTTG

GTCCTGATGGGAAGACGCATGGCAATAAGTGTGCAATGTGTGCTGAGCTG

TTTTTAAAAGAAGCTGAAAATGCCAAGCGAGAGGGTGAAACTAGAATTCG

ACGAAATGCTGAAAAGGATTTTTGCAAGGAATATGAAAAACAAGTGAGAA

ATGGAAGGCTTTTTTGTACACGGGAGAGTGATCCAGTCCGTGGCCCTGAC

GGCAGGATGCATGGCAACAAATGTGCCCTGTGTGCTGAAATTTTCAAGCA

GCGTTTTTCAGAGGAAAACAGTAAAACAGATCAAAATTTGGGAAAAGCTG

AAGAAAAAACTAAAGTTAAAAGAGAAATTGTGAAACTCTGCAGTCAATAT

CAAAATCAGGCAAAGAATGGAATACTTTTCTGTACCAGAGAAAATGACCC

TATTCGTGGTCCAGATGGGAAAATGCATGGCAACTTGTGTTCCATGTGTC

AAGCCTACTTCCAAGCAGAAAATGAAGAAAAGAAAAAGGCTGAAGCACGA

GCTAGAAACAAAAGAGAATCTGGAAAAGCAACCTCATATGCAGAGCTTTG

-continued

CAGTGAATATCGAAAGCTTGTGAGGAACGGAAAACTTGCTTGCACCAGAG

AGAACGATCCTATCCAGGGCCCAGATGGGAAAGTGCATGGCAACACCTGC

TCCATGTGTGAGGTCTTCTTCCAAGCAGAAGAAGAAGAAAAGAAAAAGAA

GGAAGGTAAATCAAGAAACAAAAGACAATCTAAGAGTACAGCTTCCTTTG

AGGAGTTGTGTAGTGAATACCGCAAATCCAGGAAAAACGGACGGCTTTTT

TGCACCAGAGAGAATGACCCCATCCAGGGCCCAGATGGAAAAATGCATGG

CAACACCTGCTCCATGTGTGAGGCCTTCTTTCAACAAGAAGAAAGAGCAA

GAGCAAAGGCTAAAAGAGAAGCTGCAAAGGAAATCTGCAGTGAATTTCGG

GACCAAGTGAGGAATGGAACACTTATATGCACCAGGGAGCATAATCCTGT

CCGTGGCCCAGATGGCAAAATGCATGGAAACAAGTGTGCCATGTGTGCCA

GTGTGTTCAAACTTGAAGAAGAAGAGAAGAAAAATGATAAAGAAGAAAA

GGGAAAGTCGAGGCTGAAAAAGTTAAGAGAGAAGCAGTTCAGGAGCTGTG

CAGTGAATATCGTCATTATGTGAGGAATGGACGACTCCCCTGTACCAGAG

AGAATGATCCTATTGAGGGTCTAGATGGGAAAATCCACGGCAACACCTGC

TCCATGTGTGAAGCCTTCTTCCAGCAAGAAGCAAAAGAAAAAGAAAGAGC

TGAACCCAGAGCAAAAGTCAAAAGAGAAGCTGAAAAGGAGACATGCGATG

AATTTCGGAGACTTTTTGCAAAATGGAAAACTTTTCTGCACAAGAGAAAT

GATCCTGTGCGTGGCCCAGATGGCAAGACCCATGGCAACAAGTGTGCCAT

GTGTAAGGCAGTCTTCCAGAAAGAAAATGAGGAAAGAAAGAGGAAAGAAG

AGGAAGATCAGAGAAATGCTGCAGGACATGGTTCCAGTGGTGGTGGAGGA

GGAAACACTCAGGACGAATGTGCTGAGTATCGGGAACAAATGAAAAATGG

AAGACTCAGCTGTACTCGGGAGAGTGATCCTGTACGTGATGCTGATGGCA

AATCGTACAACAATCAGTGTACCATGTGTAAAGCAAAATTGGAAAGAGAA

GCAGAGAGAAAAAATGAGTATTCTCGCTCCAGATCAAATGGGACTGGATC

AGAATCAGGGAAGGATACATGTGATGAGTTTAGAAGCCAAATGAAAAATG

GAAAACTCATCTGCACTCGAGAAAGTGACCCTGTCCGGGGTCCAGATGGC

AAGCACATGGCAATAAGTGTACTATGTGTAAGGAAAAACTGGAAAGGGA

AGCAGCTGAAAAAAAAAAGAAAGAGGATGAAGACAGGAGCAATACAGGAG

AAAGGAGCAATACAGGAGAAAGGAGCAATGACAAAGAGGATCTGTGTCGT

GAATTTCGAAGCATGCAGAGAAATGGAAAGCTTATCTGCACCAGAGAAAA

TAACCCTGTTCGAGGCCCATATGGCAAGATGCACATCAATAAATGTGCTA

TGTGTCAGAGCATCTTTGATCGAGAAGCTAATGAAAGAAAAAAGAAAGAT

GAAGAGAAATCAAGTAGCAAGCCCTCAAATAATGCAAAGGATGAGTGCAG

TGAATTTCGAAACTATATAAGGAACAATGAACTCATCTGCCCTAGAGAGA

ATGACCCAGTGCACGGTGCTGATGGAAAGTTCTATACAAACAAGTGCTAC

ATGTGCAGAGCTGTCTTTCTAACAGAAGCTTTGGAAAGGGCAAAGCTTCA

AGAAAAGCCATCCCATGTTAGAGCTTCTCAAGAGGAAGACAGCCCAGACT

CTTTCAGTTCTCTGGATTCTGAGATGTGCAAAGACTACCGAGTATTGCCC

AGGATAGGTTATCTTTGTCCAAAGGATTTAAAGCCTGTCTGTGGTGACGA

TGGCCAAACCTACAACAATCCTTGCATGCTCTGTCATGAAAACCTGATAC

-continued

GCCAAACAAATACACACATCCGCAGTACAGGGAAGTGTGAGGAGAGCAGC

ACCCCAGGAACCACCGCAGCCAGCATGCCCCCGTCTGACGAA

Solubility in *E. coli* BL21 (De3)

Prokaryotes produce soluble and inclusion body bound protein. Solubility is influenced by temperature, protein charge and protein structure and size. Insoluble inclusion bound protein is often misfolded, is typically inactive, and is isolated in very pure and insoluble inclusion bodies. Inclusion bound protein is isolated and re-folded in vitro, and then purified. Soluble protein is in a folded structure, is often functional and exists in the cytoplasm with the rest of proteome.

Figure 4:
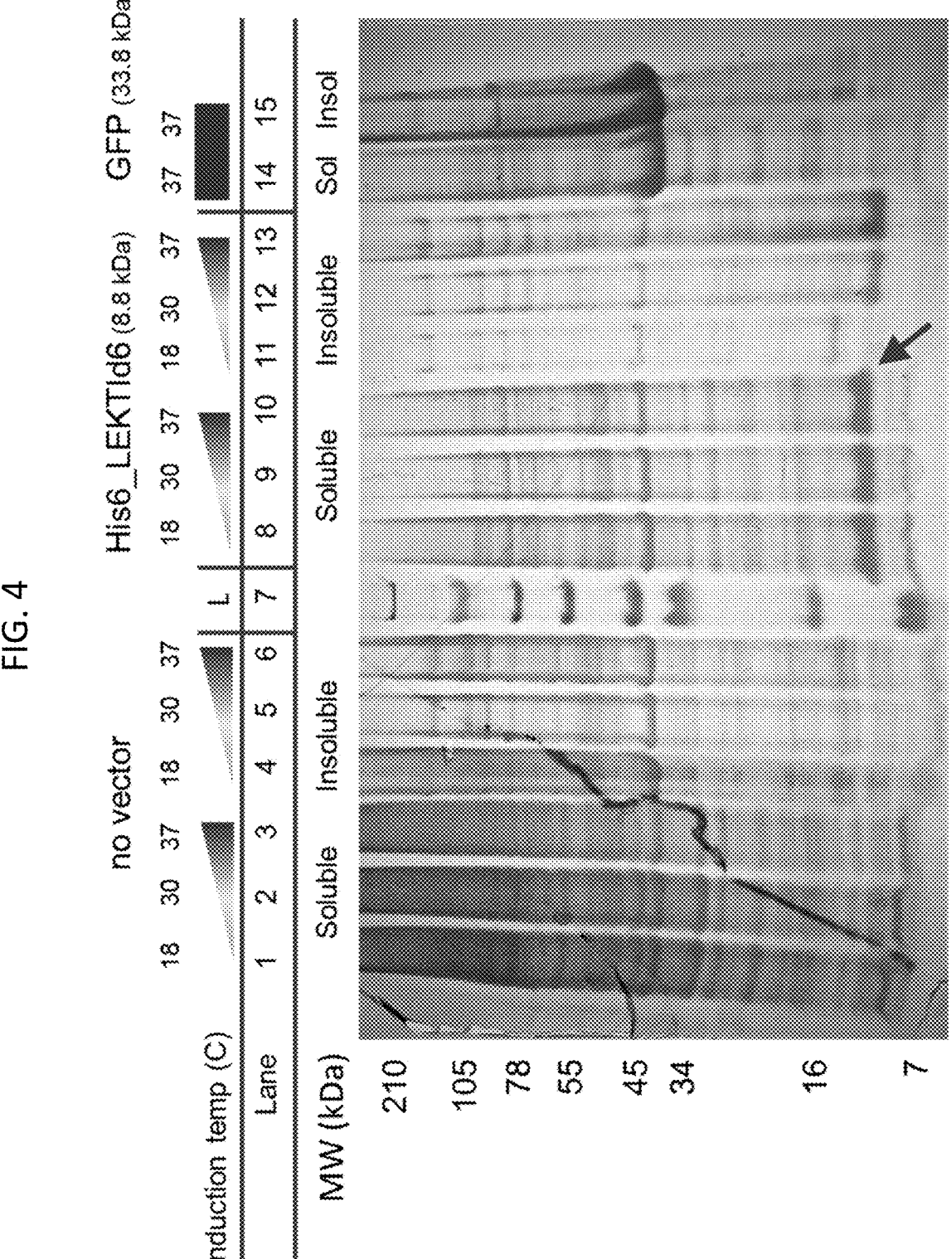
FIG. 4 shows SDS-PAGE results demonstrating that LEKTId6 is highly soluble in *E. coli* BL21 (De3).

A first set of experiments were performed to determine if domain 6 was produced reliably in *E Coli*. Soluble protein was isolated by affinity purification and buffer exchange, and then purified. Solubility test assays were used to determine the distribution between inclusion body protein and soluble protein fraction. Briefly, domain 6 protein expressing cells (*E. coli* BL21 (De3)) were lysed with aqueous buffer. High speed centrifugation and inclusion body purification were used to isolate the soluble fraction and inclusion body fraction. The isolated fractions were subjected to sodium dodecylsulphate polyacrylamide gel electrophoresis (SDS-PAGE). FIG. 4 shows results from SDS-PAGE demonstrating that LEKTId6 (8.8 kDa) was highly soluble in *E. coli* BL21 (De3). *E. coli* GFP (33.8 kDa) was used as a positive control, and no vector was used as a negative control. Experiments were performed at three different induction temperatures: 18, 30 and 37° C. As shown in FIG. 4, a band at 8.8 kDa was detected in the soluble fraction of the His6_LEKTId6 experimental group. The arrow indicates the band at 8.8 kDa.

Figure 5:
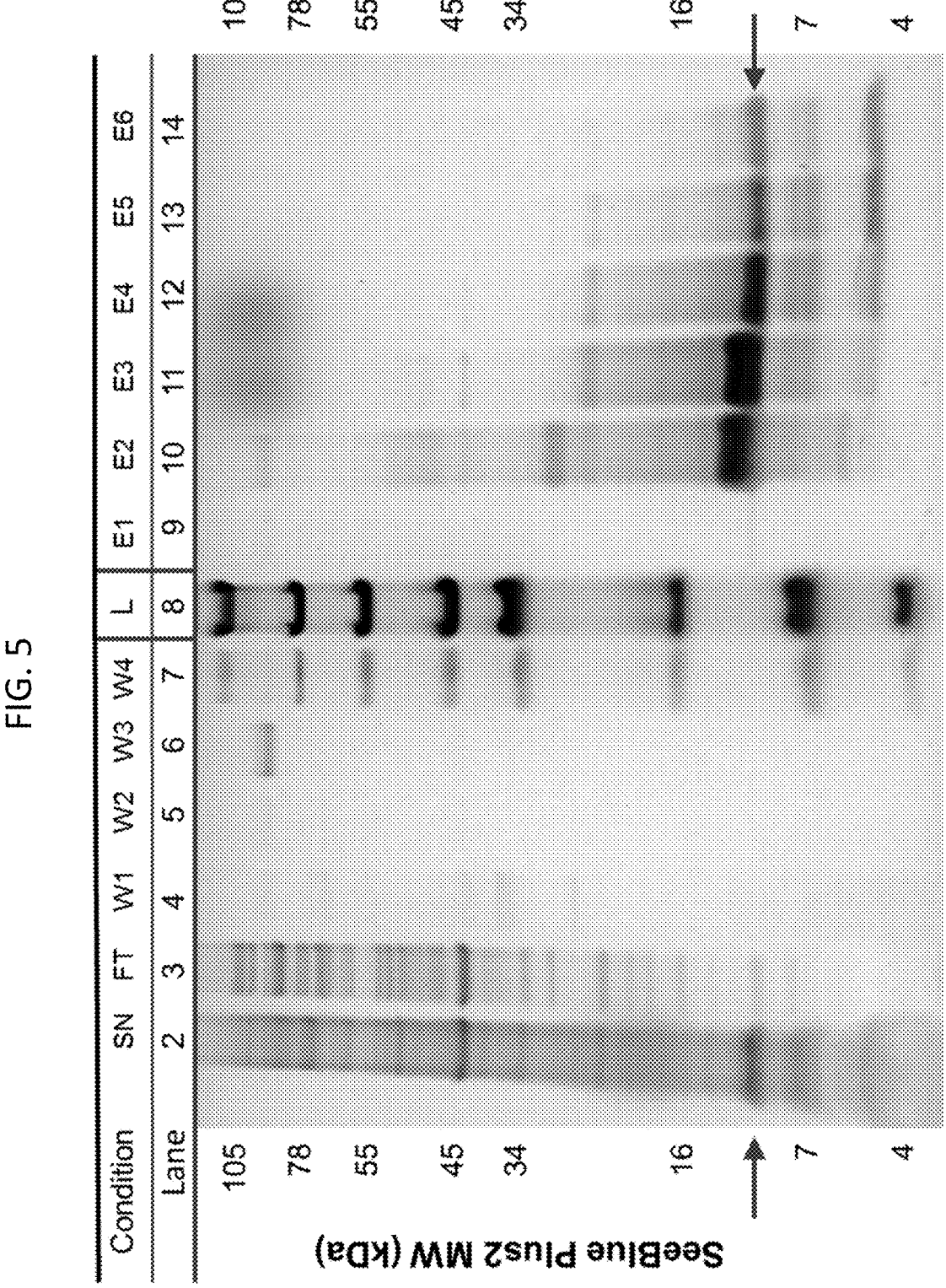
FIG. 5 shows SDS-PAGE results demonstrating successful affinity purification for H6-LEKTId6 (8.8 kDa).
Figure 6:
FIG. 6 shows SDS-PAGE results demonstrating LEKTId6-H6 (8.8 kDa) is potentially N-terminally truncated.

FIG. 5 shows results from SDS-PAGE demonstrating that affinity purification was successfully carried out for H6-LEKTId6 (8.8 kDa). The arrows indicate the band at 8.8 kDa. FIG. 6 shows that LEKTId6-H6 (8.8 kDa) may be N-terminally truncated. In both FIG. 5 and FIG. 6, the following abbreviations were used to for experimental groups:

SN=clarified cell lysate (supernatant)

FT=non-Ni2+bound protein (flow-through)

W1-4=eluents from a series of washes (1-4). Note some contamination from the neighboring ladder in W4.

L=SDS-PAGE protein ladder (SeeBlue Plus2, ThermoFisher Scientific)

E1-6=eluents from the column after imidazole treatment (i.e. the resulting affinity-purified protein). As the column is treated, different eluent fractions (1-6) were collected.

Example 5

The capacity of purified recombinant LEKTI Domain 6 (LETKId6) fragments to function in vitro as a serine protease inhibitor was assessed.

Figures 7A, 7B:
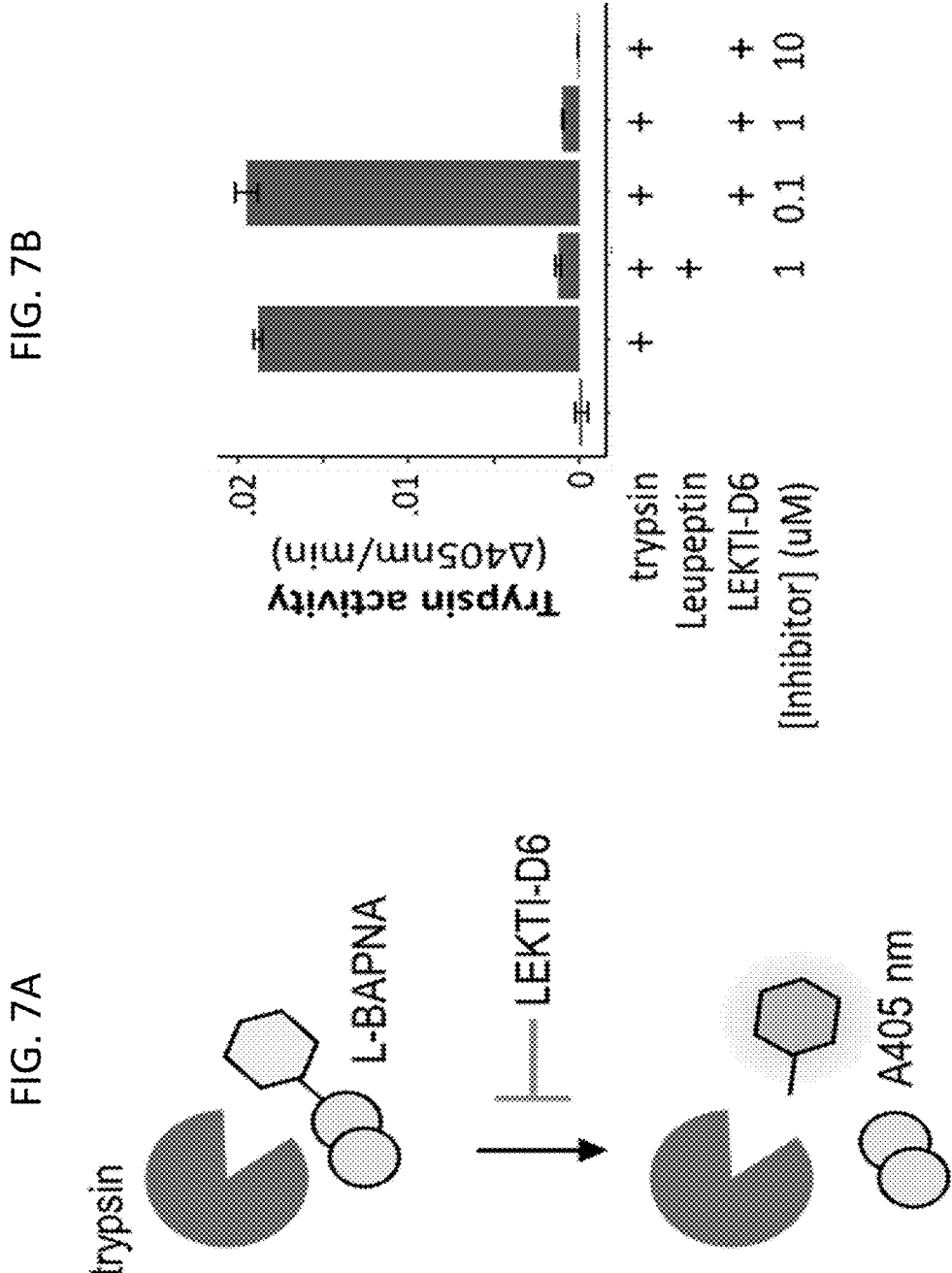
FIG. 7A and FIG. 7B show recombinantly produced LEKTI Domain 6 inhibits trypsin in vitro.

First, the ability of recombinantly produced LEKTId6 to inhibit trypsin in vitro was determined. Enzyme activity was measured using BApNA (Nα-benzoyl-1-arginine-p-nitroanilide) as substrate specific for trypsin. FIG. 7A shows a schematic overview of the assay. The assay was carried out by mixing 80 uL of LEKTId6 at concentrations (0.25, 2.5, 25 uM) with 20 uL of trypsin (35 ug/mL) and 100 uL of 2× trypsin assay buffer (100 mM Tris-HCl, pH 8.0, 300 mM NaCl, 100 mM CaCl2, 0.02% Triton-X-100, 500 UM L-BAPNA). In the reaction mixture, components were at final concentrations of of LEKTId6 (0.1, 1, 10 uM); trypsin (3.5 ug/mL), assay buffer (50 mM Tris-HCl, pH 8.0, 150 mM NaCl, 50 mM CaCl2, 0.01% Triton-X-100); and L-BAPNA (250 uM). The reaction was allowed to proceed for 15 min at 37° C. The tryspin inhibitor leupeptin was used as a positive control. The formation of product was measured at 405 nm with a microplate reader. A blank control was used. Trypsin activity was defined as the rate of change in the absorbance at 405 nm (an indicator of L-BAPNA cleavage) per minute under the established conditions. As shown in FIG. 7, LEKTI Domain 6 inhibited trypsin activity in vitro.

Figures 8A, 8B:
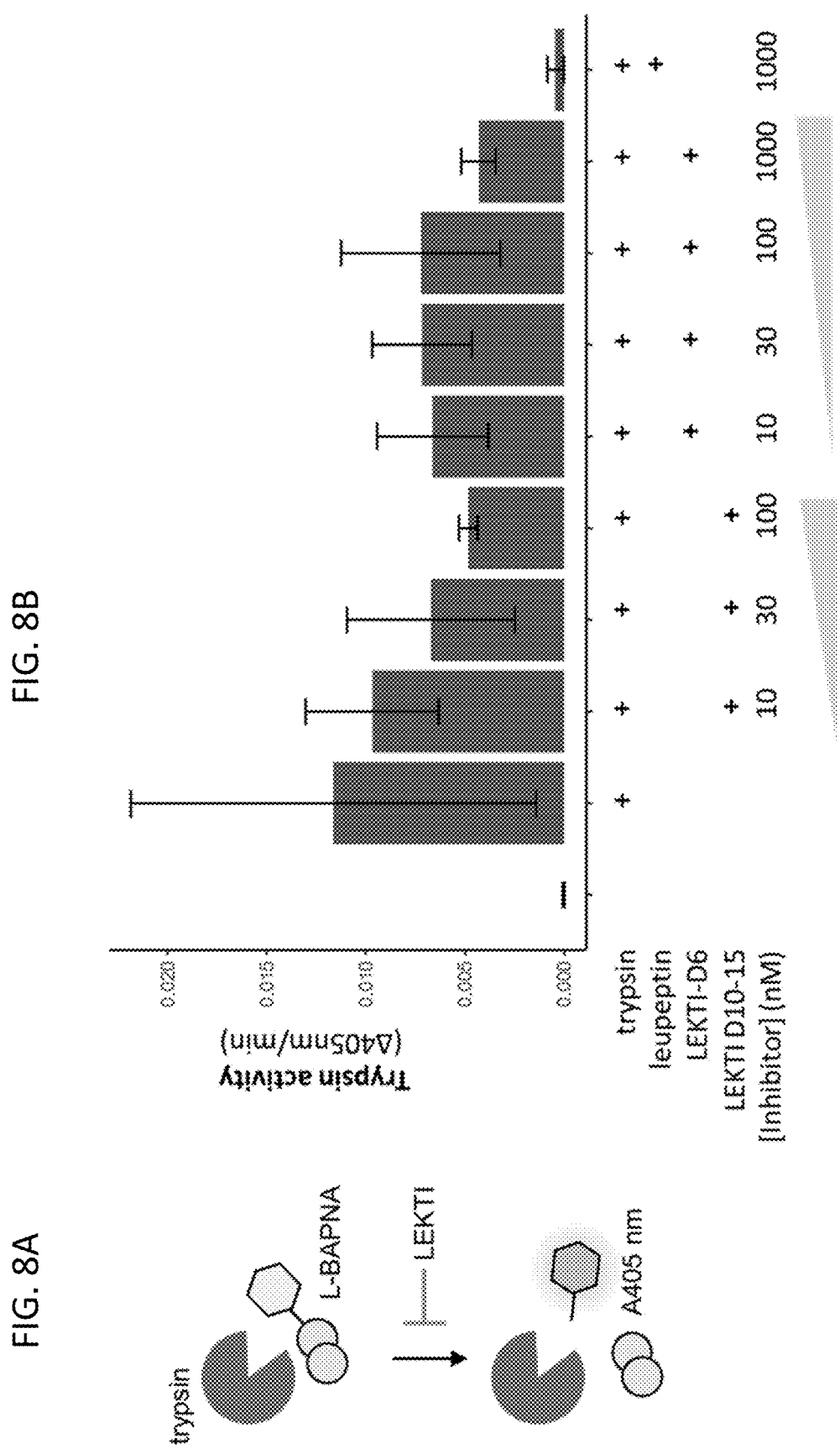
FIG. 8A and FIG. 8B show recombinantly produced LEKTI Domain 6 (ct His6 tag) inhibits trypsin in vitro compared to LEKTI domains 10-15.
Figures 9A, 9B:
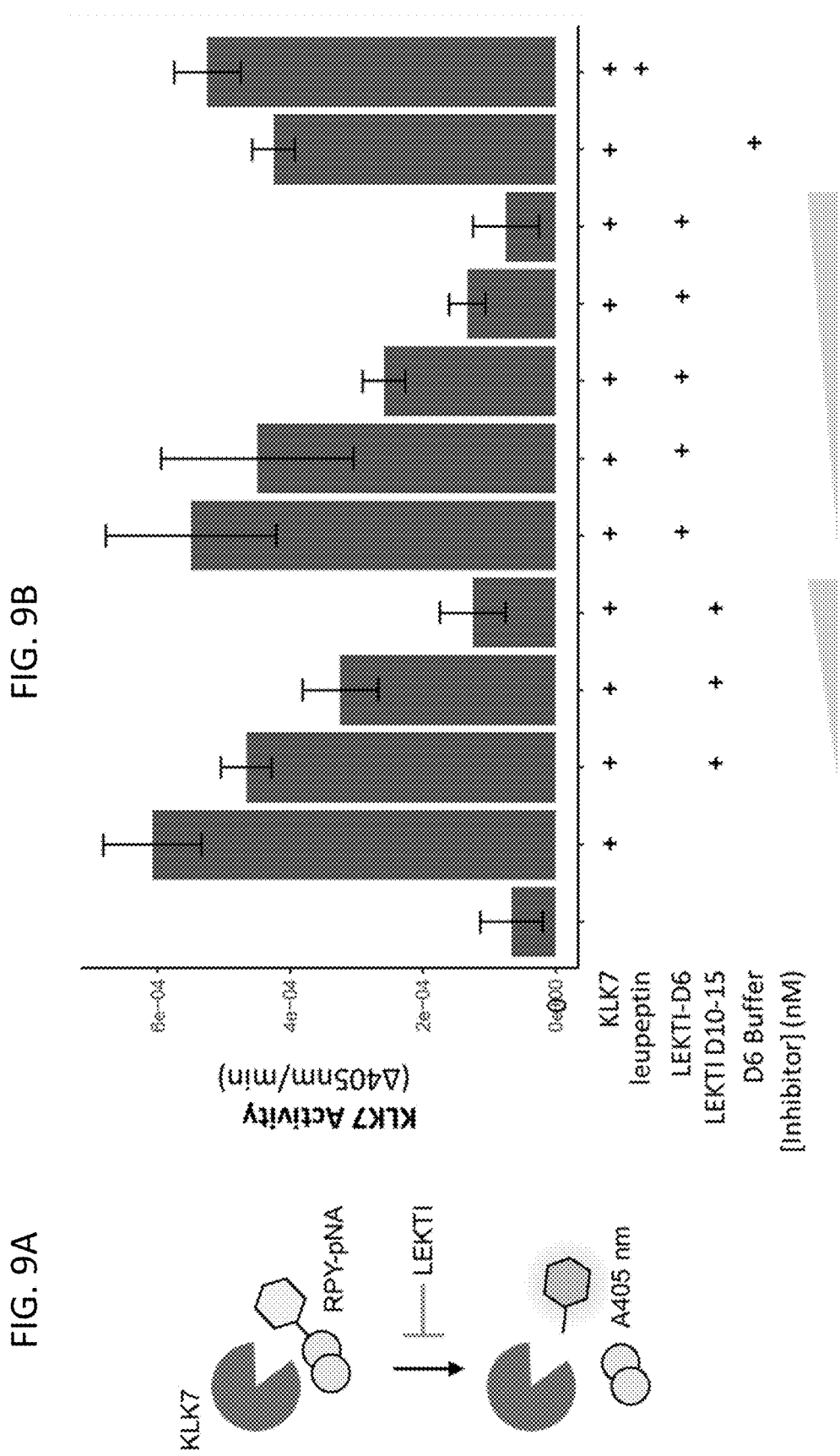
FIG. 9A and FIG. 9B show recombinantly produced LEKTI Domain 6 inhibits KLK7 in vitro similar to inhibition of KLK7 by LEKTI domains 10-15.
Figure 10B:
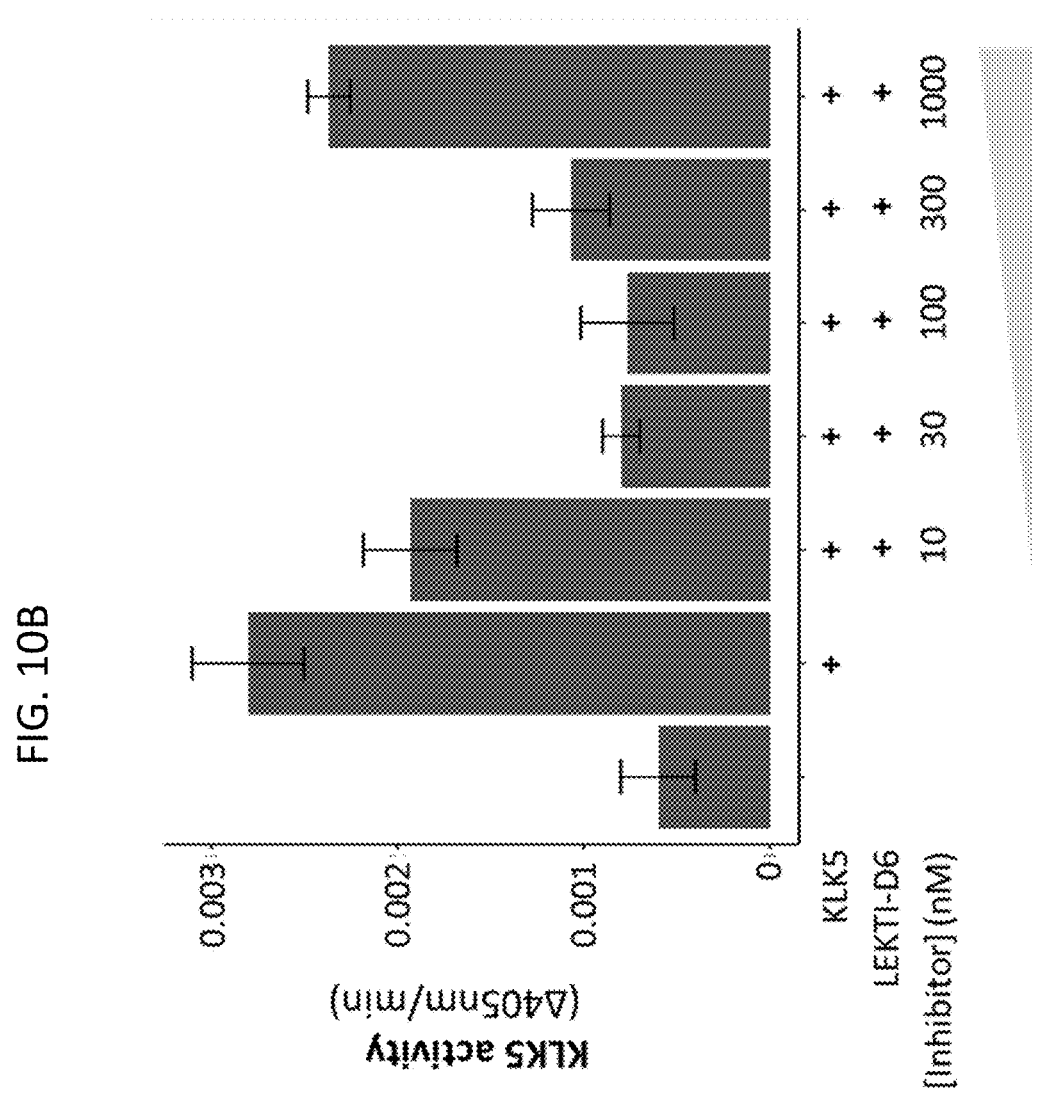
FIG. 10A and FIG. 10B show recombinantly produced LEKTI Domain 6 inhibits KLK5 in vitro at nanomolar concentrations.
Figure 10A:
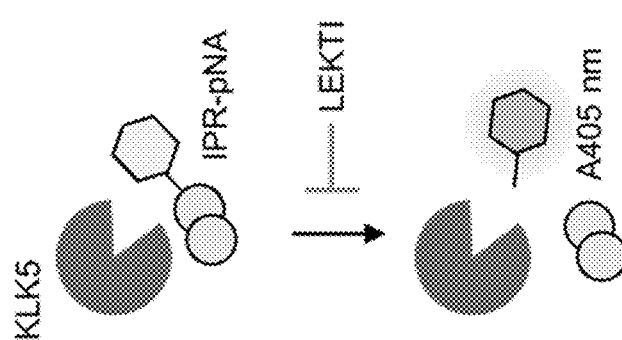

Next, the effect of LEKTI Domain 6 (ct His6 tag) on trypsin inhibition was determined and compared to the effects of LEKTI domain 10-15 on trypsin inhibition. A trypsin inhibition assay was performed as described above, where enzyme activity was measured using L-BAPNA (Nα-benzoyl-1-arginine-p-nitroanilide) as substrate specific for trypsin. FIG. 8 shows a schematic overview of the assay. LETKId6 (10, 30, 100, 1000 nm) or LEKTI domain 10-15 (10, 30, 100 nm) were mixed with L-BAPNA (final concentration 250 uM) for 10 min at 25° C. The tryspin inhibitor leupeptin was used as a positive control. The ability of recombinantly produced LEKTId6 to inhibit kallikreins 7 and 5 (KRK7 and KRK5) in vitro was determined. Briefly, proteinases KLK7 and KLK5 were incubated with increased concentrations of LEKTId6 for 5 min at 25° C. before addition of their optimal peptide substrates, which was Suc-Arg-Pro-Tyr-p-Nitro-Anilide for KLK7 and D-Ile-Pro-Arg-p-Nitro-Anilide for KLK5. The formation of product was measured at 405 nm with a microplate reader. A blank control was used. Schematic overviews of the KLK7 assay and the KLK5 assay are shown in FIGS. 9A and 10A, respectively. For KLK7, increasing concentrations of LEKTId6 (10, 30, 100, 300, 1000 nm) and increasing concentrations of LEKTId10-15 (10, 30, 100 nm) were used. The tryspin inhibitor leupeptin was used as a negative control. For KLK5, increasing concentrations of LEKTId6 (10, 30, 100, 300, 1000 nm) were used. As shown in FIG. 9B, recombinantly produced LEKTI Domain 6 inhibits KLK7 in vitro about as well as LEKTI domains 10-15. As shown in FIG. 10B, recombinantly produced LEKTId6 inhibits KLK5 in vitro at nanomolar concentrations. While, high concentrations of LETKId6 were shown to be stimulatory, without being bound by theory, this may be due to a buffer component of the assay, particularly leftover imidazole that remained in the LEKTId6 sample after affinity purification.

Example 6

Efficacy of therapeutic LETKId6 *S. epidermidis* strains will be evaluated in a condition Netherton's mouse model. Briefly, we will validate the absence of LEKTI in the skin of CRISPR created Netherton's syndrome mice (conditional SPINK5-/-) after induction of Cre recombination at 1, 2, and 4 weeks. Mice with a validated Netherton's syndrome phenotype will be treated with topical application of recombinant LEKTI to resolve skin conditions in the Spink5 conditional mutant. The rationale for first using purified LEKTI is to avoid dependency on the construction of *S. epidermidis* strains such that we can rapidly demonstrate the efficacy of topical application in vivo. Second, we will evaluate the ability of *S. epidermidis*-purified or LEKTI to demonstrate the value of probiotic colonization for sustained remediation. As controls, we will topically colonize the same mice pre-Cre-induction of the SPINK5 conditional mutation. To assess the effect of LETKId6 in the mouse model, we will perform longitudinal assays (1×/week) where possible and endpoint assays (3 weeks post-colonization) to test if application of therapeutic *S. epidermidis* will (1) produce detectable amounts of LEKTI in vivo, as measured by immunohistochemical analysis of skin (endpoint), (2) reduce skin disease severity as measured by DASI (longitudinal and endpoint), (3) improve TEWL (longitudinal) and permeability scores (endpoint), (4) ameliorate skin morphology, as measured by histological analysis (endpoint), and (5) result in changes in proteolytic activity, as measured using colorimetric assays that target KLK5 and KLK7 (endpoint).

INCORPORATION BY REFERENCE

The entire disclosure of each of the patent documents, including patent application documents, scientific articles, governmental reports, websites, and other references referred to herein is incorporated by reference herein in its entirety for all purposes. In case of a conflict in terminology, the present specification controls. All sequence listings, or Seq. ID. Numbers, disclosed herein are incorporated herein in their entirety.

The following references, to the extent that they provide exemplary procedural or other details supplementary to those set forth herein, are specifically incorporated herein by reference.

Armengot-Carbo, M. et al. (2014) "The role of filaggrin in the skin barrier and disease development." Actas Dermosifiliogr Mar; 106 (2):86-95.

Brachkova, M. I., P. Marques, J. Rocha, B. Sepodes, M. A. Duarte and J. F. Pinto (2011). "Alginate films containing *Lactobacillus plantarum* as wound dressing for prevention of burn infection." J Hosp Infect 79(4): 375-377.

Brown, S J., & McLean, W H. (2012) J. Invest. Dermatol. 132, 751-62

Chen, Y E., & Tsao, H. (2013) J. Am. Acad. Dermatol. 69, 143-155

Cheung A L, et al. (2004) "Regulation of virulence determinants in vitro and in vivo in *Staphylococcus aureus*." FEMS Immunological Medical Microbiology 40(1): 1-9

"DNA Recombination." Methods in Molecular Biology 745(XIV): 1-565.

Gross, et al, WO 94/00098 assigned to Lancaster Group AG

Gross, et al, WO 94/00109 assigned to Lancaster Group AG

Gueniche, A., P. Bastien, J. M. Ovigne, M. Kermici, G. Courchay, V. Chevalier, L. Breton and I. Castiel-Higounenc (2010). "*Bifidobacterium longum* lysate, a new ingredient for reactive skin." Exp Dermatol 19(8): 1-8.

Jeong J G et al. (2011). A Tat-grafted anti-nucleic acid antibody acquires nuclear-localization property and a preference for TAR RNA. Biochem Biophys Res Commun. Mar 18; 406(3):403-7.

Kreiswirth, B N., et al. (1983). The toxic shock syndrome exotoxin structural gene is not detectably transmitted by a prophage. Nature 305:709-712.

Lauderdale, et al. (2010). Biofilm dispersal of community-associated methicillin-resistant *Staphylococcus aureus* on orthopedic implant material. J. Orthop. Research. 28:55-61

Lee, S H., Jeong, S K. and Ahn, S K. (2006). "An update of the defensive barrier function of skin." Yonsei Med J 47(3): 293-306.

Lin, Y T., Wang, C T., and Chiang, B L. (2007). "Role of bacterial pathogens in atopic dermatitis." Clin Rev Allergy Immunol 33(3): 167-177.

Ma, J., et al. (2014) Cell-penetrating peptides mediated protein cross-membrane delivery and its use in bacterial vector vaccine. Fish & Shellfish Immunology 39 8-16

McAleer, M A., & Irvine, AD. (2013) J. Allergy Clin. Immunol. 131, 280-91.

Mitsudo K. et al., (2003) "Inhibition of Serine Proteinases Plasmin, Trypsin, Subtilisin A, Cathepsin G, and Elastase by LEKTI: A Kinetic Analysis", Biochemistry, 42, 3874-3881

Monk, I., et al. (2012) Direct transformation to manipulate genetically *Staphylococcus aureus* and *Staphylococcus epidermidis*. mBio.

Muizzuddin, N., Maher, W., Sullivan, M., Schnittger, S., and Mammone, T. (2012). "Physiological effect of a probiotic on skin." J Cosmet Sci 63(6): 385-395.

Nakanishi, N., T. Oshida, S. Yano, K. Takeda, T. Yamaguchi and Y. Ito (1986). "Construction and characterization of new cloning vectors derived from *Streptomyces griseobrunneus* plasmid pBT1 and containing amikacin and sulfomycin resistance genes." Plasmid 15(3): 217-229.

Nakatsuji, T. and R. L. Gallo (2014). "Dermatological therapy by topical application of non-pathogenic bacteria." J Invest Dermatol 134(1): 11-14.

Oehlke J et al. (1998). Cellular uptake of an alpha-helical amphipathic model peptide with the potential to deliver polar compounds into the cell interior non-endocytically. Biochim Biophys Acta. November 11; 1414(1-2): 127-39.

Ostenson C G et al. (1997). Galparan: a powerful insulin-releasing chimeric peptide acting at a novel site. Endocrinology. Aug; 138(8):3308-13.

Otsuka, A., et al. (2014) J. Allergy Clin. Immunol. 133, 139-46.el-10 (2014).

Peral, M. C, M. A. Martinez and J. C. Valdez (2009). "Bacteriotherapy with *Lactobacillus plantarum* in burns." Int Wound J 6(1): 73-81.

Peral, M. C, M. M. Rachid, N. M. Gobbato, M. A. Huaman Martinez and J. C. Valdez (2010). "Interleukin-8 production by polymorphonuclear leukocytes from patients with chronic infected leg ulcers treated with *Lactobacillus plantarum*." Clin Microbiol Infect 16(3): 281-286

Powers, M E., et al. (2011). J Bacteriol, 193:340-348

Proksch, E., J. M. Brandner and J. M. Jensen (2008). "The skin: an indispensable barrier." Exp Dermatol 17(12): 1063-1072

Remington: The Science and Practice of Pharmacy, 19th edition. Easton, PA: Mack Publishing Co., 1995

Sambrook J, et al. (1989). Molecular Cloning: A Laboratory Manual. Cold Spring Harbor Laboratory Press, New York.

Sambrook, J F., and Russell, D W., ed. (2001). Molecular Cloning: A Laboratory Manual, 3rd ed., Vols 1, 2 and 3. Cold Spring Harbor Laboratory Press Simonen, M. and I. Palva (1993). "Protein secretion in *Bacillus* species." Microbiol Rev 57(1): 109-137

Smith, E W., & Maibach, H I., (1995) Percutaneous Penetration Enhancers, CRC Press ISBN 9780849321528

Stout, T E., et al. (2014)/Invest Dermatol. 134, 423-9

The Science and Practice of Pharmacy (1995), 19th Ed. Easton, PA: Mack Publishing Co.

Volz, T., Y. Skabytska, E. Guenova, K. M. Chen, J. S. Frick, C. J. Kirschning, S. Kaesler, M. Rocken and T. Biedermann (2014). "Nonpathogenic bacteria alleviating atopic dermatitis inflammation induce IL-10-producing dendritic cells and regulatory Tr1 cells." J Invest Dermatol 134(1): 96-104

Webb, T R., & Hsu, CPS. U.S. Pat. No. 4,659,774 assigned to American Hoechst Corporation Wyman T B, et al. (1997) Design, synthesis, and characterization of a cationic peptide that binds to nucleic acids and permeabilizes bilayers. Biochemistry. March 11; 36(10):3008-17

Zhang, Y Q., et al. (2003). Genome-based analysis of virulence genes in a non-biofilm-forming *Staphylococcus epidermidis* strain (ATCC12228). Molecular Microbiology 49(6), 1577-1593

Although illustrative embodiments of the present invention have been described herein, it should be understood that the invention is not limited to those described, and that various other changes or modifications may be made by one skilled in the art without departing from the scope or spirit of the invention.

---

What is claimed is:

1. A composition for the treatment of a skin disease comprising:

a microbe genetically modified to express and provide one or more LEKTI protein domains onto the skin of a mammal, wherein the LEKTI protein domains are effective to penetrate one or more layers of the mammal's skin and effective to inhibit serine protease activity of at least one serine protease in or on the mammal's skin.

2. The composition of claim 1, wherein the microbe is adapted to live for a controlled duration on the surface of the mammal's skin to provide a continuous supply of LEKTI protein domains.

3. The composition of claim 1, wherein the LEKTI protein domains are effective to ameliorate the symptoms of Netherton Syndrome.

4. The composition of claim 1, wherein the microbe is genetically modified by transfection/transformation with a recombinant DNA plasmid encoding the LEKTI protein domains.

5. The composition of claim 1, wherein the LEKTI domains are operably linked to one or more recombinant protein domains that are effective to enhance secretion from the microbe and/or penetration of the mammal's skin.

6. The composition of claim 1, wherein at least one LEKTI domain is operably linked to a SecA domain.

7. The composition of claim 1, wherein at least one LEKTI domain is operably linked to an RMR domain.

8. The composition of claim 1, wherein at least one LEKTI domain comprises an amino acid sequence according to SEQ ID NO: 1.

9. The composition of claim 1, wherein the microbe is adapted to multiply on the skin of the mammal.

10. The composition of claim 1, wherein expression of at least one LEKTI domain is controlled by an operon and the amount of LEKTI provided to the mammal's skin is proportional to the availability of an extrinsic factor.

11. The composition of claim 1, wherein the expression of at least one LEKTI domain is controlled by a promoter that is constitutively active.

12. The composition of claim 1, wherein the microbe has been genetically modified by transfection/transformation with a recombinant DNA plasmid encoding the one or more LEKTI protein domains and one or more antibiotic resistance genes.

13. The composition of claim 1, wherein the microbe is selected from the group consisting of *Bifidobacterium, Brevibacterium, Propionibacterium, Lactococcus, Streptococcus, Staphylococcus, Lactobacillus, Enterococcus, Pediococcus, Leuconostoc,* or *Oenococcus,* and mixtures thereof.

14. A method of treating or ameliorating the effects of a skin disease of a mammal in need thereof comprising:

providing onto a surface of the skin of the mammal a microbe genetically modified to express one or more LEKTI protein domains, wherein the LEKTI protein domains are effective to penetrate one or more layers of the mammal's skin and effective to inhibit activity of at least one serine protease in or on the mammal's skin.

15. The method according to claim 14, wherein the microbe is adapted to live for a controlled duration on the surface of the mammal's skin to provide a continuous supply of LEKTI protein domains.

* * * * *